(12) United States Patent
Honma et al.

(10) Patent No.: US 8,844,556 B2
(45) Date of Patent: Sep. 30, 2014

(54) CONNECTOR AND INFUSION TUBE SET

(75) Inventors: Yasuyuki Honma, Nakakoma-gun (JP); Katsutoshi Kurose, Nakakoma-gun (JP); Yoshinori Hishikawa, Yamanashi-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 551 days.

(21) Appl. No.: 13/002,156

(22) PCT Filed: Jul. 1, 2009

(86) PCT No.: PCT/JP2009/062066
§ 371 (c)(1),
(2), (4) Date: Feb. 16, 2011

(87) PCT Pub. No.: WO2010/001939
PCT Pub. Date: Jan. 7, 2010

(65) Prior Publication Data
US 2011/0132482 A1 Jun. 9, 2011

(30) Foreign Application Priority Data

Jul. 2, 2008 (JP) ................................. 2008-173882

(51) Int. Cl.
*F24D 19/08* (2006.01)
*A61M 5/36* (2006.01)
*A61M 5/38* (2006.01)
*A61M 39/22* (2006.01)
*A61M 5/14* (2006.01)

(52) U.S. Cl.
CPC .............. *A61M 5/385* (2013.01); *A61M 5/1407* (2013.01); *A61M 5/36* (2013.01); *A61M 39/223* (2013.01)
USPC .......................................... 137/197; 137/583

(58) Field of Classification Search
CPC ...... F16K 11/08; F16K 11/0853; F16K 24/02
USPC ................... 137/197, 583, 625.47, 844, 845; 251/310; 604/407, 411, 414–416
See application file for complete search history.

(56) References Cited

U.S. PATENT DOCUMENTS 2,854,027 A * 9/1958 Kaiser et al. ............. 137/625.41
3,344,785 A * 10/1967 Hamilton ....................... 604/6.1
(Continued)

FOREIGN PATENT DOCUMENTS

| CA | 2 565 842 A1 | 5/2007 |
| EP | 1 593 405 A1 | 11/2005 |

(Continued)

OTHER PUBLICATIONS http://www.merriam-webster.com/dictionary/port. Jun. 2013.*

(Continued)

*Primary Examiner* — John Fox
*Assistant Examiner* — R. K. Arundale
(74) *Attorney, Agent, or Firm* — Buchanan, Ingersoll & Rooney PC

(57) ABSTRACT

A connector includes an inlet port into which liquid is poured and which has a first flow path for the liquid, a liquid discharge port to which a tube body is connectable and which has a second flow path discharging liquid from the first flow path to the connected tube body, a gas discharge which discharges air in the first flow path, and a blocking device which, when the liquid is poured in the first flow path, temporarily stops the liquid flow. Use of the connector involves sealing an opening section of the liquid discharge port, pouring liquid in the inlet port, causing air in the first flow path to be discharged, temporarily stopping the flow of the liquid in the first flow path, unsealing the opening section of the liquid discharge port, connecting the tube body to the liquid discharge port, and resuming flow of the liquid.

8 Claims, 28 Drawing Sheets

(56) References Cited

U.S. PATENT DOCUMENTS

| | | | | |
|---|---|---|---|---|
| 3,610,268 | A * | 10/1971 | Arutunoff | 137/119.09 |
| 3,993,062 | A * | 11/1976 | Jess | 604/126 |
| 4,223,695 | A * | 9/1980 | Muetterties | 137/173 |
| 4,298,358 | A | 11/1981 | Ruschke | |
| 4,615,694 | A * | 10/1986 | Raines | 604/126 |
| 5,045,096 | A * | 9/1991 | Quang et al. | 96/155 |
| 5,242,424 | A * | 9/1993 | Chen | 604/251 |
| 5,405,331 | A * | 4/1995 | Behnke et al. | 604/167.02 |
| 5,423,346 | A * | 6/1995 | Daoud | 137/399 |
| 5,779,674 | A * | 7/1998 | Ford | 604/126 |
| 5,916,201 | A * | 6/1999 | Wilson et al. | 604/248 |
| 7,422,565 | B2 * | 9/2008 | Delnevo et al. | 604/6.16 |
| 8,038,663 | B2 * | 10/2011 | Miner | 604/500 |
| 8,282,608 | B2 * | 10/2012 | Miner et al. | 604/251 |
| 8,366,658 | B2 * | 2/2013 | Davis et al. | 604/82 |
| 2006/0155247 | A1 | 7/2006 | Lampropoulos et al. | |

FOREIGN PATENT DOCUMENTS

| | | |
|---|---|---|
| JP | 2005-137407 A | 6/2005 |
| JP | 2007-143830 A1 | 6/2007 |
| JP | 2008-142409 A | 6/2008 |
| WO | WO 2005/028066 A1 | 3/2005 |
| WO | 2007/000066 A1 | 1/2007 |

OTHER PUBLICATIONS

International Search Report (PCT/ISA/210) issued on Oct. 6, 2009, by Japanese Patent Office as the International Searching Authority for International Application No. PCT/JP2009/062066.

Written Opinion (PCT/ISA/237) issued on Oct. 6, 2009, by Japanese Patent Office as the International Searching Authority for International Application No. PCT/JP2009/062066.

Extended European Search Report issued Oct. 17, 2013 by the European Patent Office in European Patent Application No. 09773517.9 (6 pgs).

* cited by examiner

CONNECTOR AND INFUSION TUBE SET

TECHNICAL FIELD

The present invention relates to a connector and an infusion tube set.

BACKGROUND ART

In medical implements needing connection of flow paths for liquids used in infusion, transfusion, nutrition dosing or the like, it is necessary to perform, as required, connection/disconnection of liquid flow paths (circuits) at the time of effecting sustained or momentary flow of a liquid such as a medicinal liquid, blood, fluid food, etc. In such an instance, it is known to attach a connector for connection between liquid flow paths to an intermediate part of a circuit.

Representative examples of such a connector include a three-way cock (connector) (see, for example, Patent Document 1). The connector described in Patent Document 1 has a connector body (base) having an inner cavity part (recessed part), and three tubular connection sections formed to project from the connector body. Valve bodies are disposed respectively in two of the three connection sections. In a connector having such a configuration, the two connection sections in which the valve bodies are disposed are referred to as "female-side connection sections," while the remaining connection section is referred to as a "male-side connection section." Each of the female-side connection sections is configured such that a tube body (for example, a tube or a mouth part of a syringe) can be connected thereto, and a valve body is opened or closed according to whether the tube body is connected or not connected.

In order to configure an infusion circuit by use of the connector according to Patent Document 1, an infusion bag and a tube are prepared separately, one end side of the tube is connected to the infusion bag, and the other end side of the tube is connected to, for example, one of the two female-side connection sections of the connector. As a result, an infusion circuit is configured. When the infusion circuit is used, for example, a gas-permeable cap may preliminarily be attached to (put on) the male-side connection section of the connector, whereby air in the tube and the connector can be replaced by an infusion, or priming can be performed, before use of the infusion circuit. This results in a condition in which the entire inside space of the connector, namely, the inside of the connector body and the inside of the connection sections, are filled with the infusion.

When the cap is detached in this condition, however, liquid at the inside may leak or scatter from the male-side connection section, depending on the tension between the cap and the infusion, or the internal pressure in the connector.

Patent Document 1: Japanese Laid-Open Patent Publication No. 2005-137407

SUMMARY OF THE INVENTION

An object of the present invention is to provide a connector and an infusion tube set, which ensures that, at a time of connecting a tube body to a liquid discharge port of the connector in a condition in which, for example, a tube is preliminarily connected to an inlet port of the connector and the portion ranging from the tube to the connector is filled with liquid, the liquid can securely be prevented from leaking or scattering from the liquid discharge port, and transfer of the liquid into the tube body, which is connected to the liquid discharge port, can swiftly be performed after connection of the tube body.

In order to attain the above object, according to the present invention, there is provided a connector including:

an inlet port into which a liquid is poured and which has a first flow path through which the poured liquid passes;

a liquid discharge port to which a tube body can be connected and which has a second flow path through which the liquid having passed through the first flow path is discharged into the connected tube;

gas discharge means that discharges air in the first flow path when the liquid is poured into the first flow path; and blocking means which, when the liquid is poured into the first flow path, temporarily stops flow of the liquid before the poured liquid reaches the second flow path, wherein the connector is used in such a manner that an opening section of the liquid discharge port is sealed, the liquid is poured into the inlet port with the tube body not yet connected to the liquid discharge port, thereby causing air in the first flow path to be discharged through the gas discharge means, flow of the liquid is temporarily stopped in the first flow path by the blocking means, the opening section of the liquid discharge port is unsealed while flow of the liquid is temporarily stopped, the tube body is connected to the liquid discharge port, and flow of the liquid is resumed.

This ensures that when, for example, a tube is preliminarily connected to the inlet port of the connector and liquid is poured through the tube into the inlet port, the pouring operation can be performed in a condition where the opening section of the liquid discharge port has been sealed, and the tube body is not yet connected to the liquid discharge port. When the liquid is poured into the inlet port, air in the first flow path of the inlet port is discharged through the gas discharge means, while the first flow path of the inlet port is filled with the liquid. Further, attendant on this, flow of the liquid is temporarily stopped in the first flow path by the blocking means. Then, when the tube body is connected to the liquid discharge port, the connector can be used in such a manner that the opening section of the liquid discharge port is unsealed while flow of the liquid is temporarily stopped, and the connecting operation of the connector is carried out.

When the connecting operation is carried out, the liquid has not yet entered into the second flow path of the liquid discharge port. Therefore, the liquid inside the connector (the first flow path) is securely prevented from leaking or scattering to the exterior from the second flow path. After the connecting operation is completed, flow of the liquid in the connector can be resumed.

In addition, since the liquid has already reached the first flow path of the connector, the transfer of the liquid, after completion of the connecting operation, into the tube body connected to the liquid discharge port can be carried out speedily.

Further, in the connector according to the present invention, preferably, the second flow path is filled with air in a condition where flow of the liquid is temporarily stopped.

This ensures that the liquid in the connector (the first flow path) can securely be prevented from leaking or scattering to the exterior from the second flow path.

In addition, in the connector according to the present invention, preferably, the inlet port is formed with a through-hole penetrating through a wall section that defines the first flow path, and the gas discharge means is composed of a filter member, which is disposed in the through-hole, and which is permeable to air but impermeable to liquid.

This ensures that, when air is discharged via the through-hole, the liquid is blocked by the filter member, and accordingly, the liquid can be securely prevented from flowing out unintentionally via the through-hole together with air.

Further, in the connector according to the present invention, preferably, the gas discharge means includes a gas discharge port, which projects in a direction that is different from directions of the inlet port and the liquid discharge port, and which has a third flow path through which air passes.

This ensures that, upon transition from a condition in which the liquid is not yet poured into the inlet port to a condition in which the liquid has been poured into the inlet port, air inside the inlet port is pushed by the liquid, and is passed through the third flow path and discharged toward the exterior.

In addition, in the connector according to the present invention, preferably, a filter member, which is permeable to air but impermeable to liquid, is disposed in the third flow path.

This ensures that, when air is discharged from the third flow path, the liquid flows into the third flow path together with the air, but the liquid is blocked by the filter member. Accordingly, the liquid can securely be prevented from flowing out of the third flow path unintentionally.

Further, in the connector according to the present invention, preferably, the first flow path, the second flow path and the third flow path intersect one another through an intersection part where end portions thereof intersect one another; and the blocking means is formed at the intersection part, and is composed of a cylinder section, which is cylindrical in shape, and a cock, which is inserted turnably in the cylinder section and is formed with changeover flow paths corresponding to the flow paths, wherein opening and closing of the flow paths are selected by turning the cock.

This ensures that opening and closing of each of the flow paths can be selected assuredly.

In addition, in the connector according to the present invention, preferably, the blocking means has a valve body, which is disposed at the opening section of the liquid discharge port, and which has an opening/closing section formed from an elastic material, the opening/closing section being opened/closed so that the opening section can be sealed/unsealed through deformation; and the valve body is configured such that air is enclosed in the second flow path when the first flow path is filled with the liquid, in a condition where the opening/closing section is closed, and the opening/closing section is pushed by the tube body so as to be deformed and placed in an open state when the tube body is connected to the liquid discharge port.

This ensures that the liquid discharge port can be sealed/unsealed easily and assuredly.

Further, in the connector according to the present invention, preferably, the blocking means has a cap detachably attached to the liquid discharge port; and the cap, when attached to the liquid discharge port, encloses air in the second flow path upon filling of the first flow path with the liquid, by sealing the opening section of the liquid discharge port in a liquid-tight manner, and the cap is detached from the liquid discharge port when connecting the tube body to the liquid discharge port.

This ensures that, for example, in a condition where the cap is attached to the liquid discharge port, the liquid discharge port can be sealed in a liquid-tight (gas-tight) manner. Accordingly, sterility inside the second flow path is maintained securely.

In addition, in the connector according to the present invention, preferably, the blocking means has an unsealing section, which is provided at a boundary part between the first flow path and the second flow path, and which is capable of being unsealed by rupture.

This ensures that, upon flow of the liquid into the first flow path of the inlet port, the liquid is inhibited from reaching the second flow path of the liquid discharge port, and flow of the liquid can be stopped thereby.

Further, in the connector according to the present invention, preferably, the gas discharge port is located on an opposite side from the liquid discharge port, with the inlet port disposed therebetween.

This makes it possible to change the direction of flow of the liquid from the first flow path toward the second flow path.

In addition, in the connector according to the present invention, preferably, the blocking means has a tapered section, which is provided at a boundary part between the first flow path and the second flow path, such that the inside diameter of the boundary part gradually decreases toward the side of the second flow path.

This ensures that, upon flow of the liquid into the first flow path, the liquid is temporarily inhibited securely by the tapered section from flowing toward the side of the second flow path.

Further, in the connector according to the present invention, preferably, the blocking means has a stepped section provided at a boundary part between the first flow path and the second flow path.

This ensures that, upon flow of the liquid into the first flow path, the liquid is temporarily inhibited securely by the stepped section from flowing toward the second flow path.

In addition, in the connector according to the present invention, preferably, the tapered section or the stepped section has been treated to become hydrophobic.

This ensures that, upon flow of the liquid into the first flow path, flowing of the liquid toward the second flow path can temporarily be stopped more securely.

Further, in the connector according to the present invention, preferably, an inside diameter of the second flow path is smaller than an inside diameter of the first flow path, in the vicinity of the boundary part between the first flow path and the second flow path.

This ensures that, upon flow of the liquid into the first flow path, the liquid is temporarily inhibited securely by the stepped part from flowing toward the side of the second flow path.

In addition, in the connector according to the present invention, preferably, the first flow path and the second flow path are located on the same axis.

This ensures that the liquid can flow smoothly and swiftly from the first flow path to the second flow path.

Further, in the connector according to the present invention, preferably, the first flow path and the second flow path intersect each other orthogonally.

This makes it possible for the direction of flow of the liquid from the first flow path toward the second flow path to be changed.

In addition, in the connector according to the present invention, preferably, a window part is provided through which the inside of the first flow path and/or the second flow path can be visually checked.

This ensures that, upon flow of the liquid into the connector, it is possible to check to which position of the connector the liquid has flowed.

Further, in the connector according to the present invention, preferably, a color change section, the color of which is changed when the first flow path is filled with the liquid, is provided at the boundary part between the first flow path and the second flow path.

This ensures that, upon change of the color of the color change section, it can be visually checked (confirmed) based on the color change that the liquid has filled the first flow path, or stated otherwise, that the liquid has reached (the flow of the liquid has stopped at) a position that permits the liquid to flow into the second flow path. In addition, according to the present invention, there is provided an infusion tube set including:

the connector according to the invention;

a bag-side connector having two mutually independent flow paths provided at the inside thereof, a bag-side connection section, at which ends on one side of the two flow paths are opened, and which is connected to an infusion bag, and a tube connection section, which is provided at another end of one of the two flow paths, and to which a tube can be connected, wherein the tube is connected at one end thereof to the inlet port of the connector, and is connected at the other end thereof to the tube connection section of the bag-side connector.

This ensures that, when liquid is poured into the inlet port from a tube, for example, in a condition in which the tube is preliminarily connected to the inlet port of the connector, the connector seals the opening section of the liquid discharge port, to thereby produce a condition in which the tube body is not yet connected to the liquid discharge port, whereby it is made possible to perform a pouring operation. Upon filling of the inlet port with the liquid, air in the first flow path of the inlet port is discharged by the gas discharge means while the first flow path of the inlet port is filled with the liquid. Moreover, attendant on this, flow of the liquid is temporarily stopped in the first flow path by the blocking means. Then, when the tube body is connected to the liquid discharge port, the connector unseals the opening section of the liquid discharge port in a condition in which flow of the liquid is temporarily stopped, whereby it is possible to perform the connecting operation.

When the connecting operation is performed, the liquid has not yet flowed into the second flow path of the liquid discharge port. Therefore, the liquid in the connector (the first flow path) is securely prevented from leaking or scattering to the exterior from the second flow path. After completion of the connecting operation, the connector can resume flow of the liquid.

In addition, since the liquid has already reached the first flow path of the connector, after completion of the connecting operation, transfer of the liquid into the tube body, which is connected to the discharge port, can be carried out speedily.

DESCRIPTION OF THE EMBODIMENTS

A connector and an infusion tube set according to the present invention will be described in detail below, based on preferred embodiments, as shown in the accompanying drawings.

First Embodiment

Figure 1:
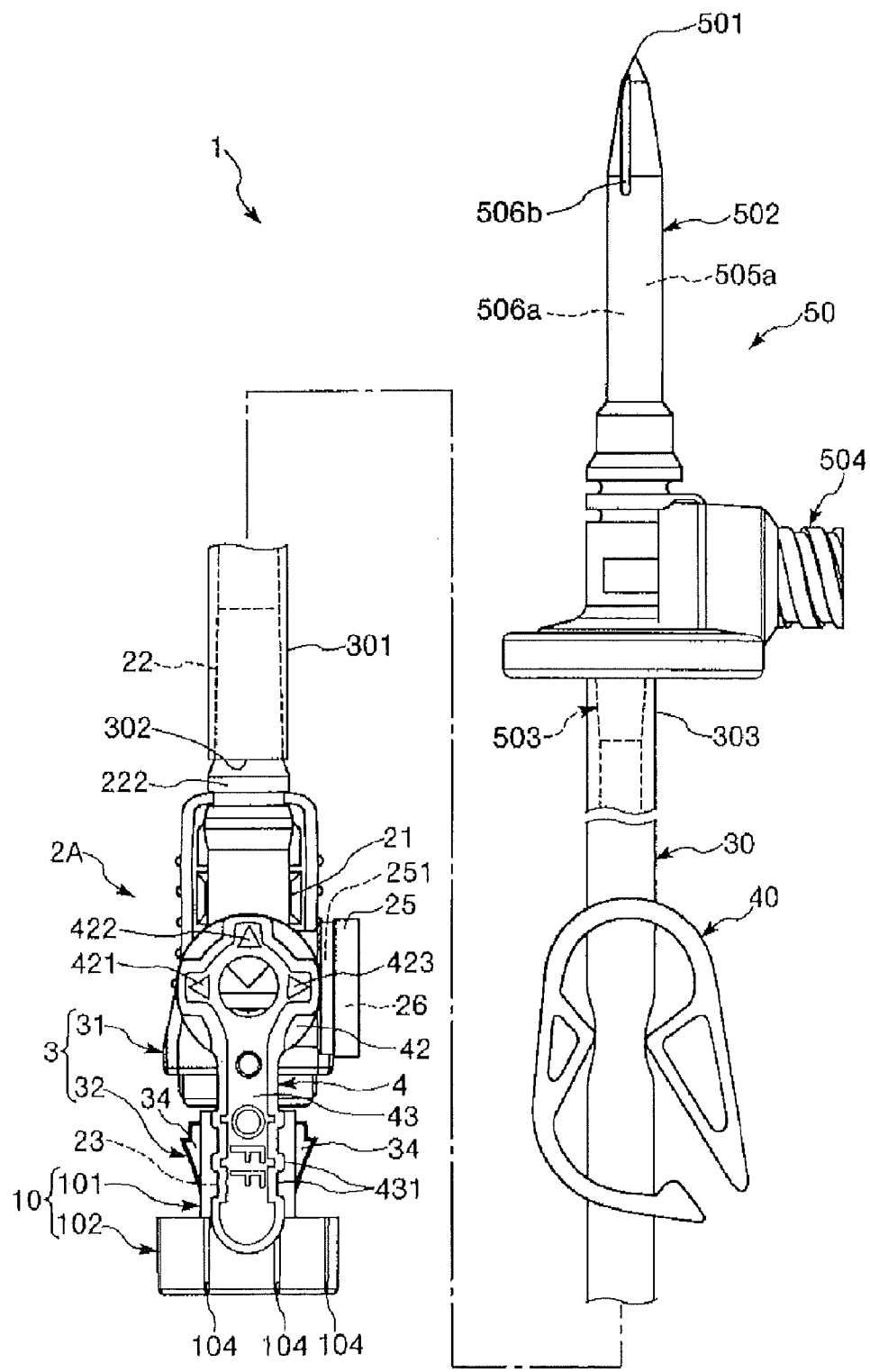
FIG. 1 is a plan view of a first embodiment of an infusion tube set according to the present invention.
Figure 2:
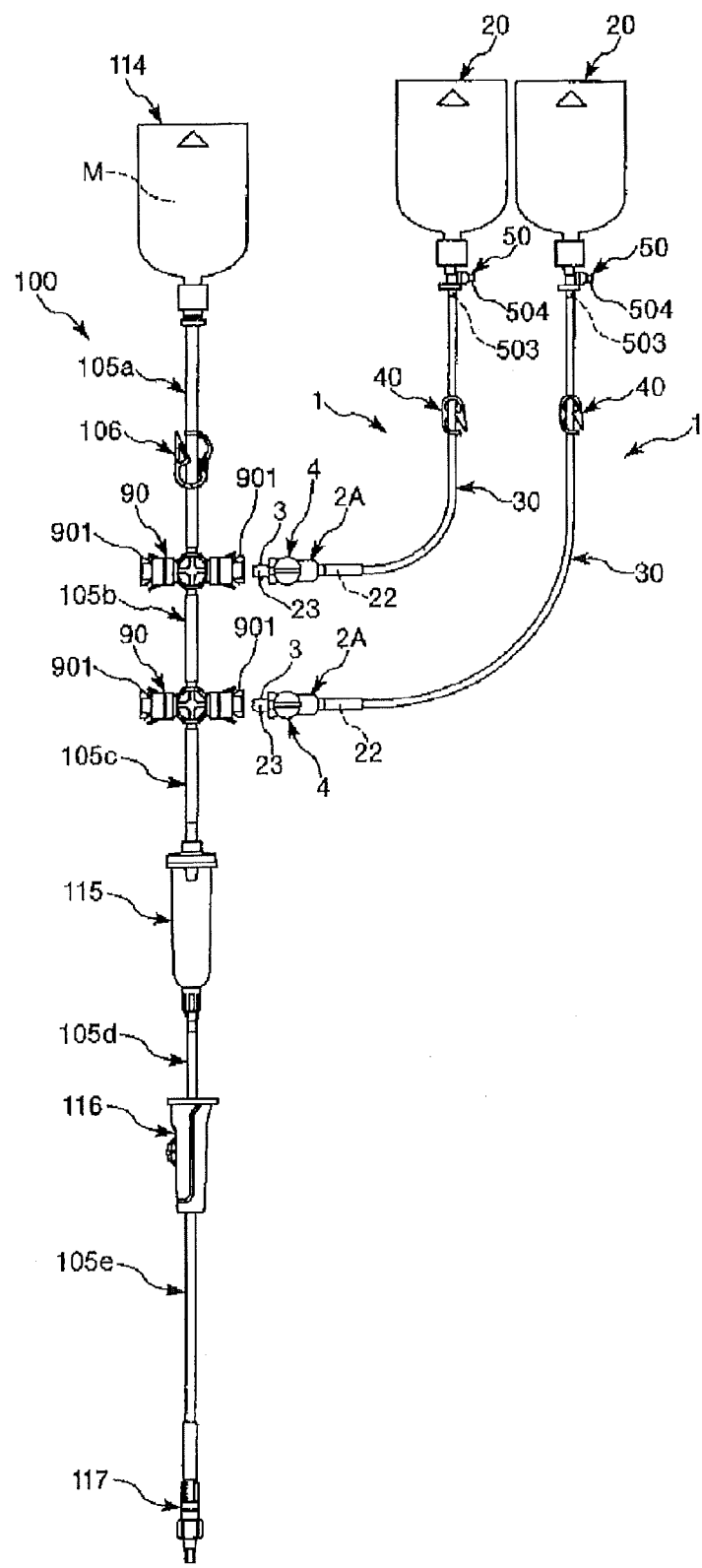
FIG. 2 is a view showing an example of a condition of use of the infusion tube set shown in FIG. 1.
Figure 3:
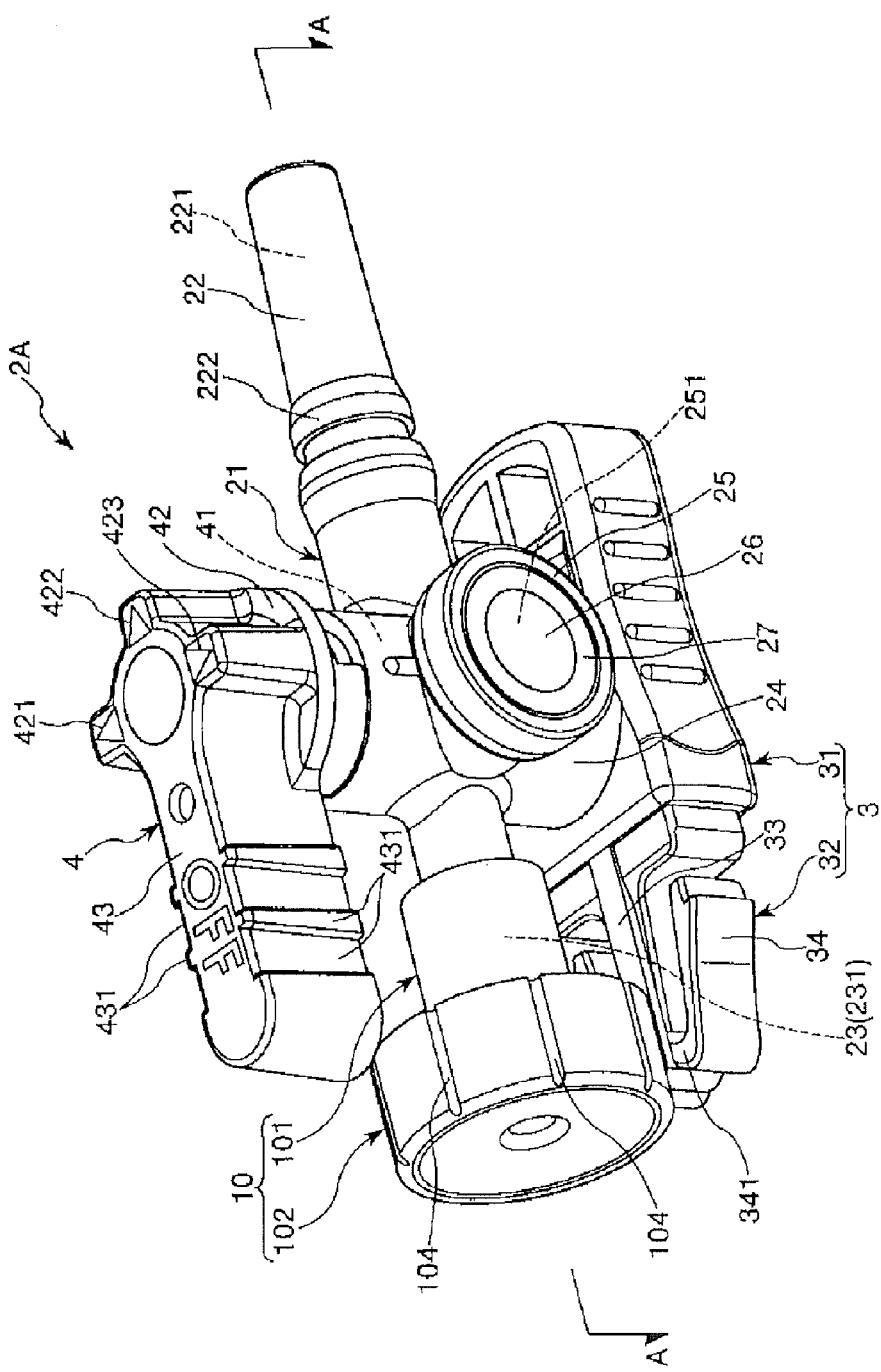
FIG. 3 is a perspective view of a first embodiment of a connector according to the present invention.
Figure 7:
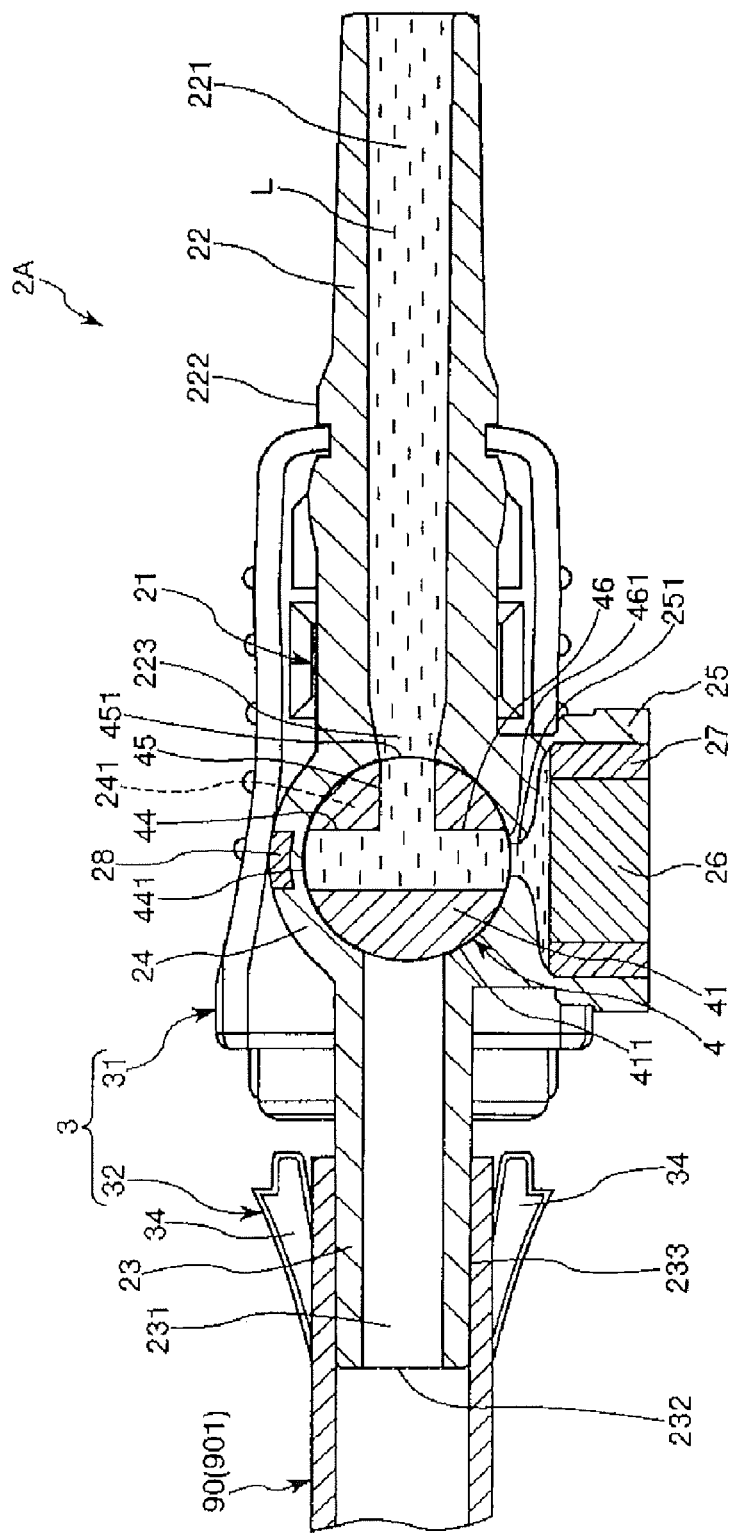
FIG. 7 is a view (a longitudinal sectional view taken along line A-A of FIG. 3) for sequentially illustrating the operation process of the connector shown in FIG. 3.
Figure 8:
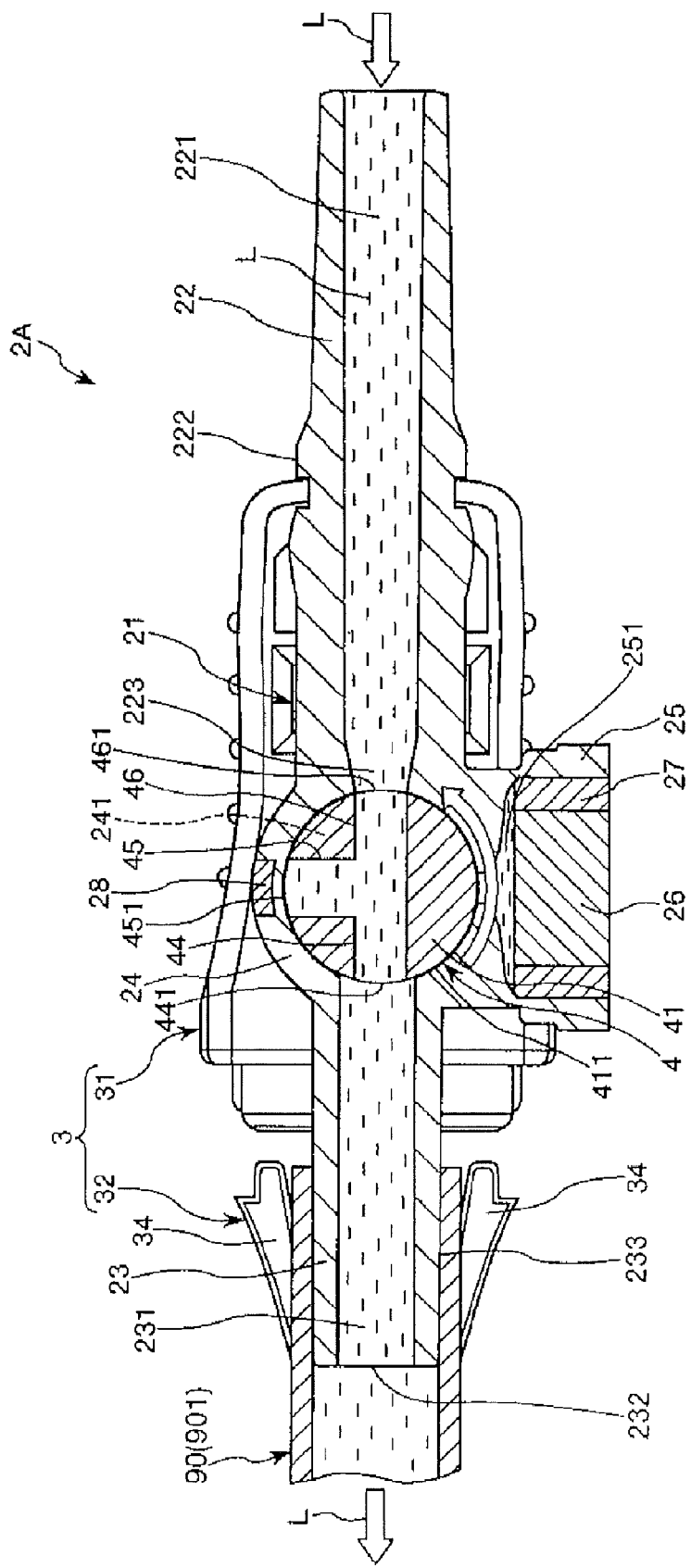
FIG. 8 is a view (a longitudinal sectional view taken along line A-A of FIG. 3) for sequentially illustrating the operation process of the connector shown in FIG. 3.
Figure 9:
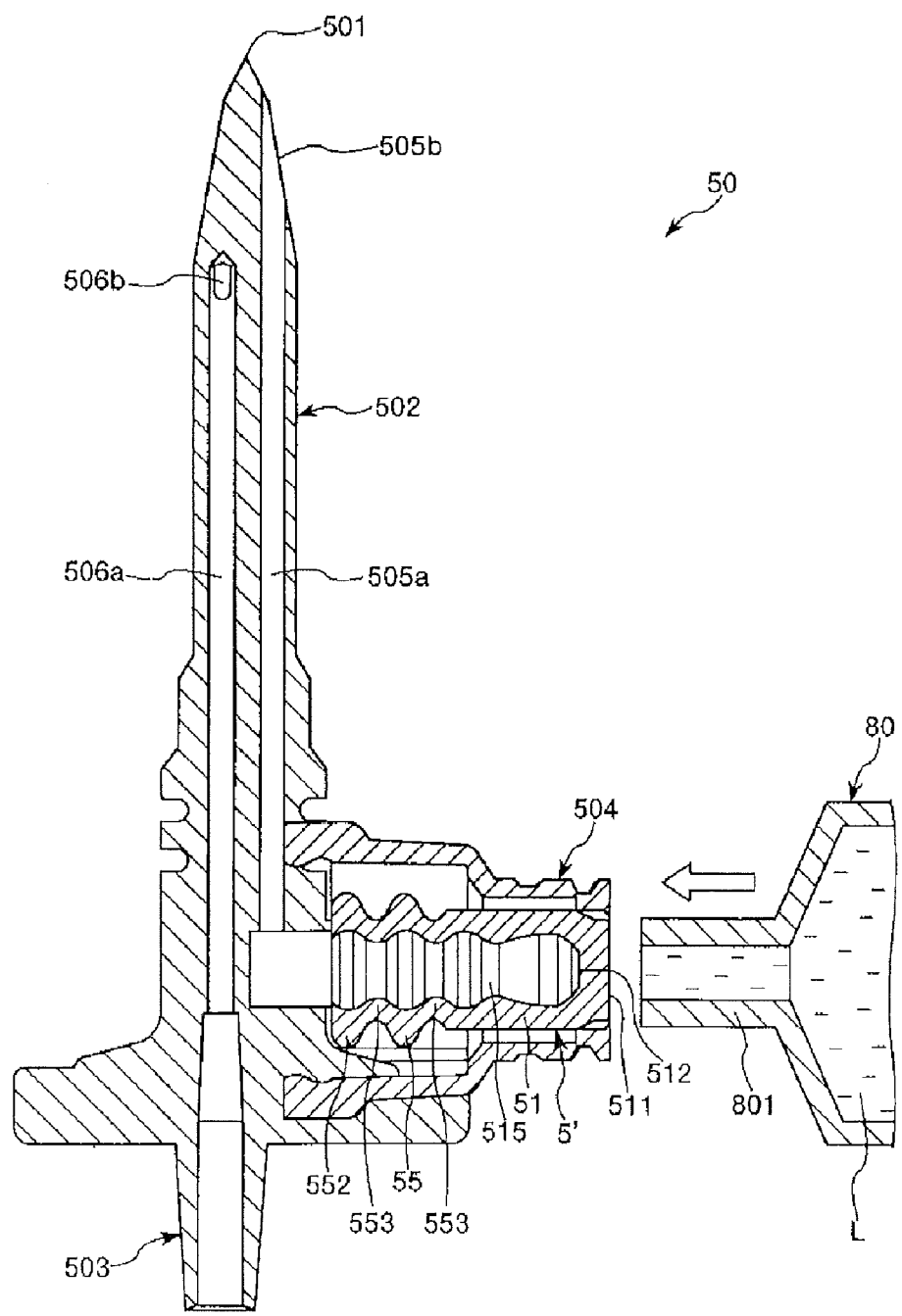
FIG. 9 is a longitudinal sectional view showing a bag-side connector in the infusion tube set shown in FIG. 1.

FIG. 1 is a plan view of a first embodiment of the infusion tube set according to the present invention, FIG. 2 is a view showing an example of a condition of use of the infusion tube set shown in FIG. 1, FIG. 3 is a perspective view of a first embodiment of the connector according to the present invention, FIGS. 4 to 8 are views (longitudinal sectional views taken along line A-A of FIG. 3) for sequentially illustrating an operation process of the connector shown in FIG. 3, and FIG. 9 is a longitudinal sectional view of a bag-side connector in the infusion tube set shown in FIG. 1. Incidentally, in the following explanations, for convenience of description, the upper side in FIGS. 1 and 2 and 9 will be referred to as "proximal (end)" or "upper," the lower side will be referred to as "distal (end)" or "lower," the right side in FIGS. 3 to 8 will be referred to as "proximal (end)," and the left side will be referred to as "distal (end)."

As shown in FIG. 1, the infusion tube set (infusion set) 1 according to the present invention is a device (set) for pouring (administering) an infusion (liquid) L into a living body (patient).

The infusion tube set 1 has a bag-side connector 50 located on an upstream side and connected to an infusion bag 20, a connector 2A according to the present invention, which is located on a downstream side relative to the bag-side connector 50, and a tube 30 for connecting the bag-side connector 50 and the connector 2A to each other. In addition, the tube 30 may be equipped at an intermediate portion thereof with a clamp 40 for closing the intermediate portion. The clamp 40 is configured so as to press the tube 30 from the outside in a pinching manner, thereby closing under pressure the inside of the tube 30.

In the infusion tube set 1 configured in the foregoing manner, in a condition where the clamp 40 is removed, medicinal liquid L flows from the bag-side connector 50 into the connector 2A through the tube 30. Having flowed into the connector 2A, the medicinal liquid L passes through the connector 2A and is discharged.

Before describing the connector 2A of the present invention, the bag-side connector 50 and the tube 30 will be described.

The bag-side connector 50, as shown in FIGS. 1 and 9, includes a connector body (bag connection section) 502 having a sharp needle point 501 at an upper end thereof, a tube connection section 503 provided at a lower end portion (other end portion) of the connector body 502, and a syringe connection section 504 provided at an outer peripheral portion of the connector body 502.

As shown in FIG. 1, the connector body 502 is composed of a hollow body, with an infusion inflow path 505a and an infusion outflow path 506a being formed inside thereof. The connector body 502 can pierce through a stopper (not shown), which is composed of an elastic material, in the infusion bag 20, thus permitting the bag-side connector 50 to be connected to the infusion bag 20.

The infusion inflow path 505a is a flow path through which the medicinal liquid L in a prefilled syringe 80 is transferred into the infusion bag 20, which is capable of storing the medicinal liquid L. An upper end opening section 505b of the infusion inflow path 505a opens at an outer peripheral portion of the connector body 502. The infusion inflow path 505a and the inside of the infusion bag 20 communicate with each other through the upper end opening section 505b, whereby the medicinal liquid L can flow into the infusion bag 20. In addition, the infusion inflow path 505a has a rectilinear form along the longitudinal direction of the connector body 502. Incidentally, the prefilled syringe 80 implies a syringe that is preliminarily filled with a medicinal liquid L.

The infusion outflow path 506a is a flow path through which the medicinal liquid L, which is stored (reserved) in the infusion bag 20, is transported into the tube 30. An upper end opening section 506b of the infusion outflow path 506a opens at an outer peripheral portion of the connector body 502, on a lower side relative to the upper end opening section 505b of the infusion inflow path 505a. The infusion outflow path 506a and the inside of the infusion bag 20 communicate with each other through the upper end opening section 506b, whereby the medicinal liquid L in the infusion bag 20 can flow out into the infusion outflow path 506a.

The infusion inflow path 505a and the infusion outflow path 506a, as mentioned above, do not intersect each other, that is, they are independent from each other.

The tube connection section 503 is provided at a lower end portion of the infusion outflow path 506a. The tube connection section 503 is a tubular part. A proximal portion 303 of the tube 30 can be connected to the tube connection section 503 (see FIG. 1). This allows the inside of the tube 30 and the infusion outflow path 506a to communicate with each other.

The syringe connection section 504 is provided at a lower end portion of the infusion inflow path 505a. The syringe connection section 504 is a tubular part, which projects toward a lateral side (the right side in FIG. 9). A mouth section 801 of the prefilled syringe 80 can be connected to the syringe connection section 504. This allows the inside of the prefilled syringe 80 and the infusion inflow path 505a to communicate with each other.

In addition, a valve body 5' formed of an elastic material and having a self-closing property is disposed inside the syringe connection section 504. The configuration of the valve body 5' is substantially the same as that of a valve body 5, which shall be described later, and therefore, a detailed description of the valve body 5' is omitted. When the mouth section 801 of the prefilled syringe 80 is inserted into the syringe connection section 504, the valve body 5' is deformed under pressing by the mouth section 801, so as to be brought into an open state. This allows the medicinal liquid L to flow into the infusion inflow path 505a via the mouth section 801 of the prefilled syringe 80.

Incidentally, the material for forming the bag-side connector 50 (exclusive of the valve body 5') is not particularly limited. Examples of suitable materials include various hard resin materials including polyolefins such as polyethylene, polypropylene, ethylene-vinyl acetate copolymer, etc., polyurethane, polyamides, polyesters, polycarbonates, polybutadiene, and polyvinyl chloride.

A distal portion 301 (one end side) of the tube 30 is connected to an inlet port 22 of the connector 2A, to be described later, and a proximal portion 303 (other end side) of the tube 30 is connected to the tube connection section 503 of the bag-side connector 50. Medicinal liquid L that flows out from the bag-side connector 50 is supplied into the connector 2A through the tube 30.

Incidentally, the tube 30 is formed from a flexible material. The material for forming the tube 30 is not particularly limited. Examples of suitable materials include flexible polyvinyl chloride, ethylene-vinyl acetate copolymer, polyethylene, polypropylene, polybutadiene, etc., and materials consisting mainly of any of these polymers.

Next, the connector 2A according to the present invention will be described.

The connector 2A shown in FIGS. 1 and 3 to 8 has a connector body 21, which is tubular in shape, a lock member 3 disposed on an outer peripheral side of the connector body 21, and a cap (sealing member) 10, which is connected detachably to a distal portion of the connector body 21.

As shown in FIGS. 5 to 8, the connector body 21 is a member, which is tubular in shape, and which defines therein a flow path through which the medicinal liquid L passes.

As shown in FIG. 1, the connector body 21 has a proximal portion (a portion on the proximal side) functioning as an inlet port 22, to which a distal portion 301 of the tube 30 is connected, and into which the medicinal liquid L that has passed through the tube 30 is poured. The inlet port 22 has a tapered shape such that the outside diameter of a portion on the proximal side thereof gradually decreases along the proximal direction.

In addition, the inside of the inlet port 22 forms a first flow path 221 through which the medicinal liquid L, which is poured in from the infusion bag 20 and through the tube 30, passes. The inside diameter of the portion of the first flow path 221, exclusive of a distal portion 223 thereof, is substantially constant along the longitudinal direction. The inside diameter of the distal portion 223 of the first flow path 221 gradually decreases along the distal direction.

The inlet port 22 is formed at an outer peripheral portion thereof with an enlarged diameter section 222 having an enlarged outside diameter. As shown in FIG. 1, the distal portion 301 of the tube 30 can be connected to the inlet port 22 until the distal end 302 of the tube 30 abuts against the enlarged diameter section 222. This ensures that the amount of insertion of the inlet port 22 into the tube 30 is sufficient. Accordingly, the inlet port 22 is securely prevented from slipping off from the tube 30 unintentionally.

As shown in FIG. 8, the connector body 21 has a distal portion (a portion on the distal side) functioning as a liquid discharge port 23 for discharging the medicinal liquid L that has passed through the first flow path 221. The liquid discharge port 23 is constant in both outside and inside diameter along the longitudinal direction thereof.

Figure 4:
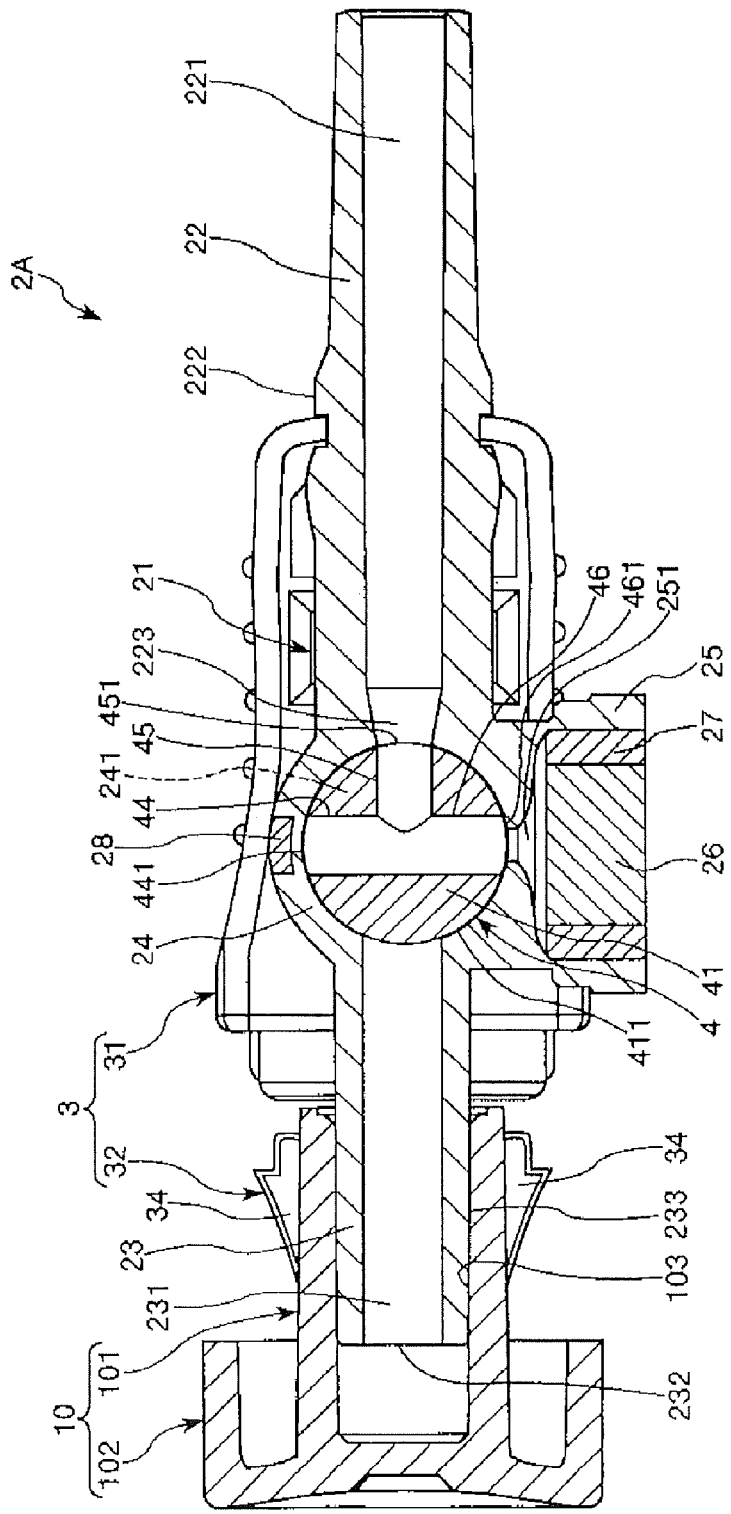
FIG. 4 is a view (a longitudinal sectional view taken along line A-A of FIG. 3) for sequentially illustrating an operation process of the connector shown in FIG. 3.
Figure 5:
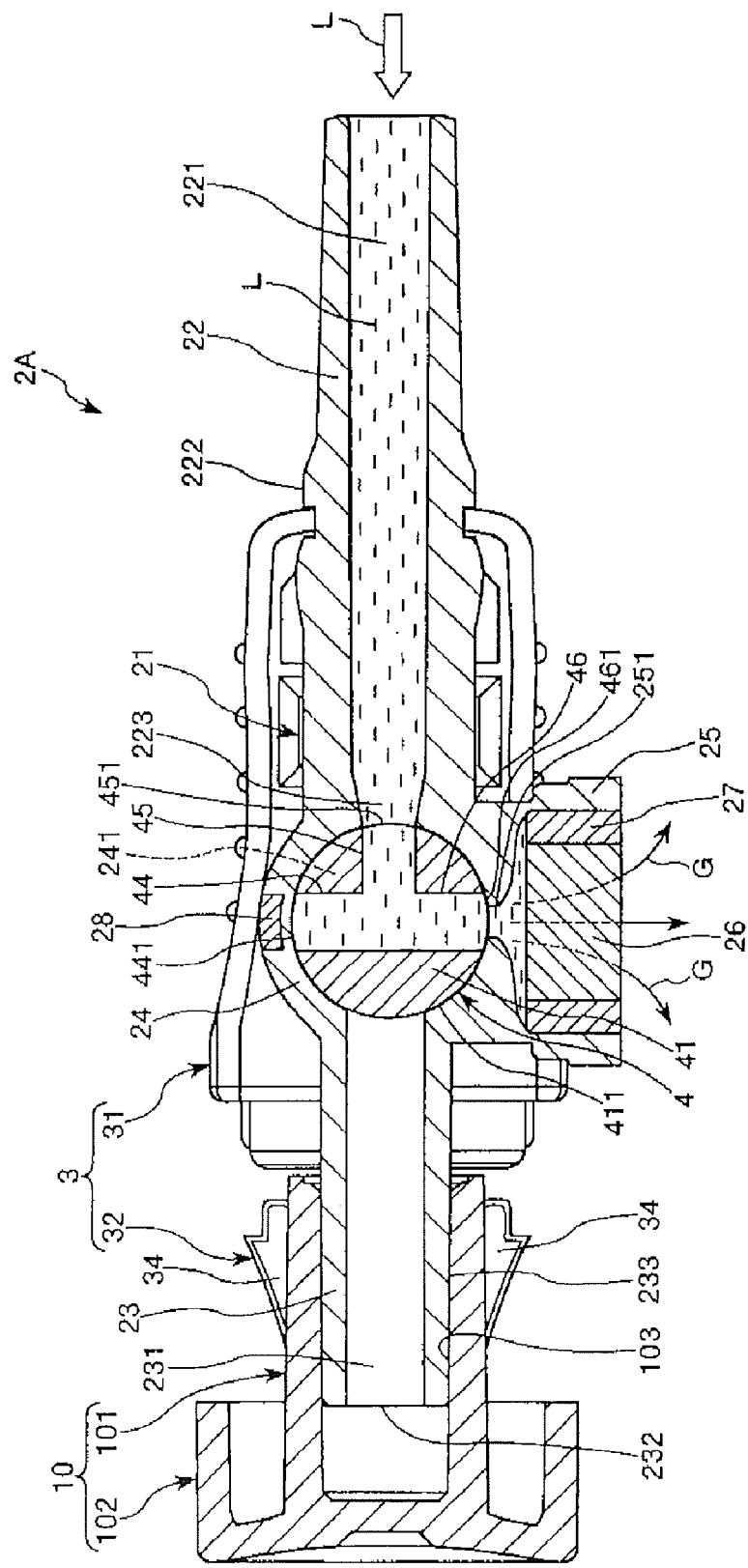
FIG. 5 is a view (a longitudinal sectional view taken along line A-A of FIG. 3) for sequentially illustrating the operation process of the connector shown in FIG. 3.

The cap 10 is attached to the liquid discharge port 23 until the medicinal liquid L is permitted to pass through the second flow path (liquid discharge flow path) 231, which is formed in the liquid discharge port 23 (see FIGS. 4 and 5). With the cap 10 removed, a tubular section (tube body) 901 of a connector 90, which is possessed by an infusion system 100 (see FIG. 2) to be described later, can be connected thereto, so that the inside of the tubular section 901 and the second flow path 231 can communicate with each other, and the medicinal liquid L can be discharged from the second flow path 231 into the tubular section 901 (see FIGS. 7 and 8).

As shown in FIG. 3, the cap 10 forms a member that is connected detachably to the liquid discharge port 23. The cap 10 includes a cap body 101 having a bottomed tubular shape, and a grip part 102 provided on the outer peripheral side of the cap body 101.

An inner peripheral portion 103 of the cap body 101 has a tapered shape, such that the inside diameter thereof gradually increases along the proximal direction. When the cap 10 is attached to the liquid discharge port 23, the inner peripheral portion 103 of the cap body 101 fits into an outer peripheral portion 233 of the liquid discharge port 23, at a portion thereof where the inside diameter becomes equal to the outside diameter of the liquid discharge port 23 (see FIGS. 4 and 5). This ensures that the cap 10, in a state of being mounted to the liquid discharge port 23 (mounted state), can seal an opening section 232 of the liquid discharge port 23 in a liquid-tight (gas-tight) manner. Accordingly, a sterile state inside the second flow path 231 can be securely maintained.

The grip part 102 is a ring-shaped member that is provided on the outer peripheral side of the cap body 101 concentrically with the cap body 101. When the cap 10, which is in the mounted state, is dismounted, the grip part 102 is gripped and is pushed along the distal direction, whereby the dismounting operation can be carried out. The grip part 102 is provided in an outer peripheral portion thereof with a plurality of grooves 104 extending in the longitudinal direction. This ensures that when the grip part 102 is gripped, the fingers can be prevented from slipping off from the grip part 102.

As shown in FIGS. 4 to 8 (also shown in FIG. 3), a cylinder section 24, which is cylindrical in shape, is formed at a central portion (intermediate portion) of the connector body 21, and more specifically, between the inlet port 22 (the first flow path 221) and the liquid discharge port (discharge port) 23 (the second flow path 231). The cylinder section 24 is disposed relative to the connector body 21, in such a manner that a center axis thereof orthogonally intersects the center axis of the connector body 21. The first flow path 221 and the second flow path 231 are positioned at the same height and communicate with a lumen 241 of the cylinder section 24.

In addition, the cylinder section 24 is formed at an outer peripheral portion thereof with a gas discharge port 25, which projects in a direction orthogonal to (different from) the inlet port 22 and the liquid discharge port 23. The gas discharge port 25 is tubular in shape, and defines therein a third flow path (gas discharge flow path) 251 through which air (gas) G passes. The third flow path 251 communicates with the lumen 241 of the cylinder section 24 at the same height as the first flow path 221 and the second flow path 231.

As shown in FIGS. 4 and 5, upon transition from a condition in which the first flow path 221 is not yet filled with the poured medicinal liquid L (the condition shown in FIG. 4) to the condition in which the first flow path 221 is filled with the poured medicinal liquid L (the condition shown in FIG. 5), air G in the first flow path 221 is pushed by the medicinal liquid L so as to pass through the third flow path 251 and be discharged to the exterior. Thus, the gas discharge port 25 functions as a gas discharge means for discharging air G in the first flow path 221.

Further, a filter member 26 is fixed to the gas discharge port 25, and more specifically, to the third flow path 251 through a fixing member 27. The filter member 26 is permeable to air G but impermeable to the medicinal liquid L. Incidentally, a configuration may be adopted in which the fixing member 27 is omitted and the filter member 26 is sealed directly in the third flow path 251.

When air G is discharged, the medicinal liquid L flows into the third flow path 251 together with the air G, but is blocked by the filter member 26. Consequently, the medicinal liquid L can securely be prevented from unintentionally flowing out through the gas discharge port 25. In addition, in cases where the medicinal liquid L is a medicine (e.g., a carcinostatic) that has a high probability of polluting the skin if the skin (e.g., the hand, a fingertip, or the like) were directly touched thereby, pollution of the skin surface with the medicinal liquid L is securely prevented by the filter member 26.

Incidentally, the filter member 26 preferably has a surface, which has been hydrophobically treated, or which is a hydrophobic film. Examples of materials capable of constituting the hydrophobic film include polytetrafluoroethylene (PTFE), a copolymer of tetrafluoroethylene and hexafluoroethylene (FEP), a copolymer of tetrafluoroethylene and perfluoroalkyl vinyl ether (PFA), polychlorotrifluoroethylene (PCTFE), polyvinylidene fluoride (PVDF), a copolymer of ethylene and tetrafluoroethylene (ETFE), a copolymer of ethylene and chlorotrifluoroethylene (ECTFE), and polypropylene (PP). For forming the filter member 26, porous materials obtained by methods such as drawing, microphase separation, electron beam etching, sintering, argon plasma particle etching, etc., are used. In addition, the method of rendering the material hydrophobic is not particularly limited. Examples of suitable methods include a method of coating the surface of the filter member 26 with a hydrophobic constituent material.

The fixing member 27 is ring-shaped. The fixing member 27 has an outside diameter set slightly greater than the inside diameter of the tubular gas discharge port 25, and an inside diameter set slightly smaller than the outside diameter of the filter member 26, which is disk-like in shape. With the fixing member 27 located between the gas discharge port 25 and the filter member 26, the filter member 26 is fixed securely to the gas discharge port 25 through the fixing member 27, so that the filter member 26 is prevented from slipping off from the gas discharge port 25.

As mentioned above, the first flow path 221, the second flow path 231, which is located coaxially with respect to the first flow path 221, and the third flow path 251, which orthogonally intersects the first flow path 221 and the second flow path 231, communicate with one another through the lumen 241 of the cylinder section 24. More specifically, the first flow path 221, the second flow path 231 and the third flow path 251 have end portions thereof that intersect one another through the lumen 241 of the cylinder section 24. In the connector 2A, the lumen 241 of the cylinder section 24 forms an intersection where the first flow path 221, the second flow path 231 and the third flow path 251 intersect one another.

As shown in FIGS. 4 to 8, the connector 2A is configured such that open/closed states of the first flow path 221, the second flow path 231 and the third flow path 251, or the communicating/non-communicating states among the first flow path 221, the second flow path 231 and the third flow path 251, can be changed. The connector 2A is provided with a cock 4 as a means for changing the communicating/non-communicating states of the flow paths.

As shown in FIG. 3, the cock 4 is composed of a trunk part 41, a base part 42, and a lever 43.

The trunk part 41 is in the shape of a solid cylinder or a hollow cylinder (a solid cylinder is shown in FIGS. 4 to 8), and is turnably inserted (fitted) in the lumen 241 of the cylinder section 24 in a gas-tight or liquid-tight manner. Therefore, the outside diameter of the trunk part 41, in a condition where the cock 4 has been drawn out from the cylinder section 24, is preferably set slightly larger (for example, by about 1 to 6%) than the inside diameter of the aforementioned cylinder section 24. In addition, an outer peripheral surface 411 of the trunk part 41 is preferably smooth. This ensures that, when the trunk part 41 is rotated, rotation thereof can be performed smoothly.

As shown in FIGS. 4 to 8, changeover flow paths (paths) of the inlet port 22, the liquid discharge port 23 and the gas discharge port 25, which correspond to the first flow path 221, the second flow path 231 and the third flow path 251, are formed in a T-shape inside the trunk part 41. More specifically, three flow paths 44, 45 and 46 extending in radial directions of the trunk part 41 at angular intervals of 90° are formed to communicate with one another in the vicinity of a central portion of the trunk part 41. In addition, the flow paths 44 to 46 are formed at height positions conforming to those of the first flow path 221, the second flow path 231 and the third flow path 251 of the inlet port 22, the liquid discharge port 23, and the gas discharge port 25.

The flow paths 44 to 46 have openings 441, 451 and 461 therein, which open at an outer peripheral surface 411 of the trunk part 41, and which are circular in shape. Incidentally, the diameters of the openings 441 to 461 are preferably equal to one another, but may be different from one another.

At an upper portion of the trunk part 41, the disk-shaped base part (lever support part) 42, having an outside diameter greater than the outside diameter of the trunk part 41, preferably is formed as one body with the trunk part 41. The base part 42 is in a state of being exposed to the upper side of the cylinder section 24.

In addition, as shown in FIG. 3, the base part 42 is provided, at a portion on the upper side in the figure, with markers 421, 422 and 423 for indicating the opening directions of the openings 441, 451 and 461. The markers 421 to 423 are provided at positions corresponding to the openings 441 to 461, namely, on the upper side of the flow paths 44 to 46, as shown in FIG. 3. Further, each of the markers 421 to 423 is in the shape of an isosceles triangle. The markers 421 to 423 are disposed such that vertexes of the isosceles triangles are oriented in the opening directions of the corresponding openings 441 to 461.

On the outer peripheral side of the base part 42, the lever 43, which projects and extends in a direction reverse to the flow path 45, preferably is formed as one body with the base part 42. The lever 43 is gripped with the fingers, and a torque is applied thereto, whereby the cock 4 is turned. Accordingly, both side surface portions of the lever 43 are provided with projections-and-recesses 431 for preventing slipping. Incidentally, in the present invention, the lever 43, which is used to perform the turning operation, is not limited to one that extends in one direction as shown in the figure. A lever that extends in two or more directions, or other handle-like levers, may also be adopted.

In addition, in the present embodiment, the cock 4 is configured so as to be freely turnable by 360° relative to the cylinder section 24, but the invention is not limited to this configuration. In other words, the connector 2A may be provided with a restricting means (not shown), which restricts the range of the turning angle of the cock 4 relative to the cylinder section 24. The restricting means can be composed, for example, of projecting portions, which are formed respectively on the cylinder section 24 and the base part 42, and which can engage with each other.

By turning the cock 4 having such a configuration, opening and closing of the first flow path 221, the second flow path 231 and the third flow path 251 can be selected.

Figure 6:
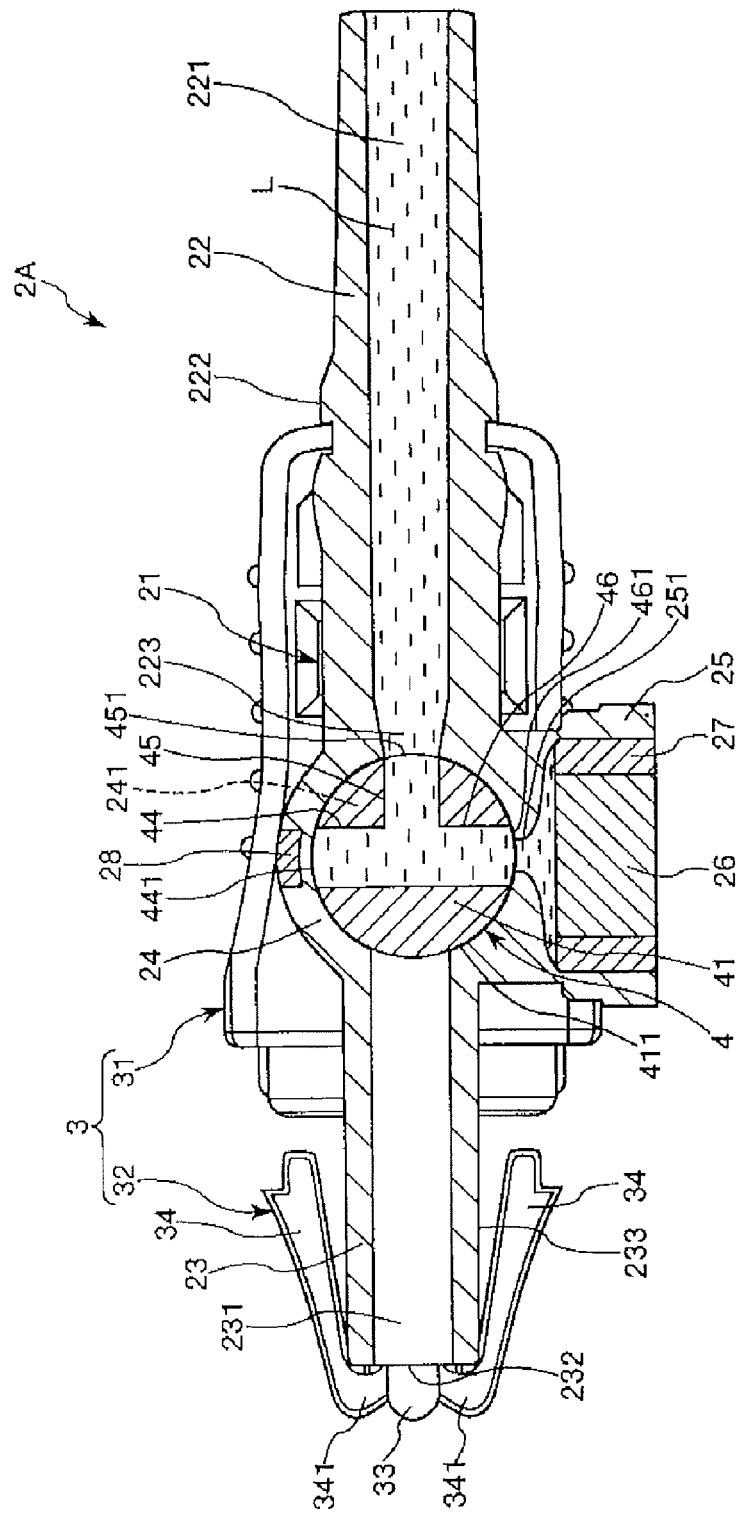
FIG. 6 is a view (a longitudinal sectional view taken along line A-A of FIG. 3) for sequentially illustrating the operation process of the connector shown in FIG. 3.

For example, in a case where the position of the lever 43 of the cock 4 is set in the same direction as the liquid discharge port 23, as shown in FIGS. 1 and 3, the first flow path 221 of the inlet port 22 and the third flow path 251 of the gas discharge port 25 are brought into communication with each other through the flow paths 45 and 46 formed in the trunk part 41 of the cock 4, whereas the second flow path 231 of the liquid discharge port 23 is sealed by the outer peripheral surface 411 of the trunk part 41, as shown in FIG. 4 (and as shown in FIGS. 5 to 7). This results in the inlet port 22 and the gas discharge port 25 being placed in a communicating state, whereas the liquid discharge port 23 is in a closed state. Hereinafter, this condition will be referred to as a "first condition (initial condition)."

In addition, in a case where the position of the lever 43 of the cock 4 is set in the same direction as the gas discharge port 25, the first flow path 221 of the inlet port 22 and the second flow path 231 of the liquid discharge port 23 are brought into communication with each other through the flow paths 44 and 46 formed in the trunk part 41 of the cock 4, whereas the third flow path 251 of the gas discharge port 25 is sealed by the outer peripheral surface 411 of the trunk part 41, as shown in FIG. 8. This results in the inlet port 22 and the liquid discharge port 23 being placed in a communicating state, whereas the gas discharge port 25 is in a closed state. Hereinafter, this condition will be referred to as a "second condition."

As shown in FIGS. 4 to 7, in the initial condition, when the medicinal liquid L is poured from the tube 30 into the first flow path 221 of the inlet port 22, the poured medicinal liquid L flows down through the first flow path 221, and while pushing the air G in the first flow path 221 toward the downstream side, flows through the flow path 45 in the cock 4 and into the flow paths 44 and 46. The medicinal liquid L, having flowed into the flow path 46, reaches the third flow path 251 of the gas discharge port 25. As a result of the medicinal liquid L having flowed into the third flow path 251 of the gas discharge port 25, the air G in the first flow path 221 is discharged through the filter member 26 in the gas discharge port 25. When most of the air G has been discharged, flow of the medicinal liquid L in the connector 2A, or stated otherwise, pouring of the medicinal liquid L into the first flow path 221 of the inlet port 22 from the tube 30, is stopped. Such a stopped condition is maintained until the second condition (the condition shown in FIG. 8) is established by turning the cock 4. Thus, in the connector 2A, when the medicinal liquid L is poured into the first flow path 221, flow of the medicinal liquid L is temporarily stopped before the medicinal liquid L reaches (flows into) the second flow path 231 of the liquid discharge port 23. Therefore, in the connector 2A, the cock 4 and the cylinder section 24 of the connector body 21, in which the trunk part 41 of the cock 4 is fitted, constitute a blocking means (stopping means), which, when the medicinal liquid L is poured into the first flow path 221, temporarily stops flow of the poured medicinal liquid L before the medicinal liquid L reaches the second flow path 231.

In addition, the blocking means is configured such that opening and closing of the first flow path 221, the second flow path 231 and the third flow path 251 can be selected by a simple operation of rotating the cock 4. Therefore, a changeover (transfer) from the first condition to the second condition can be carried out easily and assuredly. Moreover, the timing at which the flow paths are changed can be judged (determined) after the operator of the cock 4 has confirmed that flow of the medicinal liquid L has been stopped. Accordingly, the connector 2A is excellent in operability.

The material constituting the connector 2A (exclusive of the filter member 26) having such a configuration is not particularly limited. Examples of suitable materials include various resins such as polyvinyl chloride, polyethylene, polypropylene, cyclic polyolefins, polystyrene, poly-(4-methylpentene-1), polycarbonate, acrylic resin, acrylonitrile-butadiene-styrene copolymer, polyesters such as polyethylene terephthalate, polyethylene naphthalate, etc., butadiene-styrene copolymer, and polyamides (e.g., 6-nylon, 6,6-nylon, 6,10-nylon, 12-nylon). Among these materials, resins such as polypropylene, cyclic polyolefins and polyesters are preferable because they are easy to mold and are low in water vapor permeability.

In particular, the material constituting the connector body 21 is preferably substantially transparent for securing visibility of the inside thereof. This ensures that the inside of the first flow path 221 and the second flow path 231 can be visually checked through a wall part (tube wall) of the connector body 21, so that it can be checked to which part of the connector body 21 the medicinal liquid L in the connector body 21 (connector 2A) has reached. Consequently, changing from the first condition to the second condition can be securely performed by operating the cock 4, after it has been confirmed that the first flow path 221 has been filled with the medicinal liquid L and that flow of the medicinal liquid L has been stopped. Thus, the wall part of the connector body 21 functions as a window, for enabling visual inspection of the inside of the first flow path 221 and the second flow path 231.

In addition, as shown in FIGS. 4 to 8, at an outer peripheral portion of the cylinder section 24 of the connector body 21, a color change section 28 is disposed on an opposite side of the center axis from the gas discharge port 25. The color change section 28 is composed of a small piece, and is fixed to the outer peripheral portion of the cylinder section 24 of the connector body 21 by, for example, adhesion (adhesion with an adhesive or a solvent).

The color change section 28 shows a color change due to a temperature change (temperature rise, or temperature fall) thereof. The material of this section is not specifically restricted, and examples of the material include materials such as tetrahalogeno-complexes and nitrogen-containing ligand complexes.

Such a color change section 28 normally exhibits a fall in temperature through heat absorption when the first flow path 221 of the inlet port 22 is filled with the medicinal liquid L. This results in the color change section 28 showing a change in color, as compared to the color thereof before the temperature fall. Based on such a color change, it is possible to visually check (confirm) that the first flow path 221 has been filled with the medicinal liquid L, or in other words, that the medicinal liquid L has come to a position that permits flow into the second flow path 231 (i.e., flow of the medicinal liquid L has been stopped). In this case, transfer from the first condition to the second condition can be securely performed by operating the cock 4.

As shown in FIG. 3, the lock member 3 is disposed on the lower side of the cylinder section 24 of the connector body 21. The lock member 3 is used depending on the configuration (shape) of a mating body connected to the liquid discharge port 23 from which the cap 10 has been dismounted. More specifically, in some cases, the lock member 3 is connected (coupled) to the mating body, and in other cases, the lock member 3 is not connected (coupled) to the mating body. In the present embodiment, the connector 90 of the infusion system 100, which serves as the mating body, has a part that can be connected to the lock member 3. Therefore, the lock member 3 is connected to the connector 90 together with the liquid discharge port 23. This results in the connector 2A and the connector 90 becoming firmly connected to each other.

The lock member 3 has a long base section 31 and a lock section 32, which is formed to project at a distal portion of the base section 31.

The base section 31 is a section that is plate-like in shape. When the connector 2A is placed on a support base such as a table, the connector 2A is placed with the base section 31 on the lower side thereof. This ensures that the connector 2A is stably placed on the support base.

The lock section 32 has a shaft part 33, which is rod-like in shape, and a pair of claw parts 34 formed on both sides of the shaft part 33.

The shaft part 33 is formed so as to project in the distal direction.

The claw parts 34 are disposed opposite to each other, with the shaft part 33 being disposed therebetween. In addition, each of the claw parts 34 is platelet-like in shape, a distal portion 341 thereof being coupled to a distal portion of the shaft part 33. This ensures that the claw parts 34 are elastic, and can be moved closer to and away from each other. When the lock member 3 is coupled to the connector 90 of the infusion system 100, the claw parts 34 can engage respectively with predetermined parts of the connector 90.

Incidentally, the lock member 3 may be formed as one body with the connector body 21, or may be configured so that it can be attached to and detached from the connector body 21.

Next, a method of operating (method of using) the infusion tube set 1 (connector 2A) will be described below, taking a case of connecting the infusion tube set 1 to the infusion system 100 as an example.

First, the infusion system 100 will be described.

The infusion system 100 shown in FIG. 2 includes an infusion bag 114, two connectors 90, a drip tube (drip chamber) 115, a roller forceps 116, and a connector 117, with these members being laid out in this order from an upstream side. In addition, the members are interconnected through tubes 105a, 105b, 105c, 105d and 105e. Further, a clamp 106 is attached to an intermediate portion of the tube 105a.

The infusion bag 114 has an infusion M preliminarily stored therein. The infusion M may be the same as or different from the medicinal liquid L in the infusion bag 20 of the infusion tube set 1.

Each of the connectors 90 has a part, namely, a tubular section 901, which is configured so that the liquid discharge port 23 of the connector 2A of the infusion tube set 1 can be connected thereto.

The drip tube 115 is formed from a substantially transparent material so that, when the medicinal liquid L flows into the drip tube 115, the flow rate of the medicinal liquid L can be visually checked. In addition, the drip tube 115 can reserve air G that flows into the drip tube 115 together with the medicinal liquid L, whereby the air G can be prevented from flowing downstream.

The roller forceps 116 is a member for adjusting the flow rate of the medicinal liquid L.

The connector 117 is configured so that it can be connected to an indwelling needle (not shown), which is preliminarily set indwelling in a patient.

The clamp 106 is a member for closing the tube 105a. When the clamp 106 is opened, the medicinal liquid L is permitted to pass through the tube 105a.

The infusion system 100 having such a configuration is used in a condition in which the infusion bag 114 is suspended, so that the infusion bag 114 is located on a vertical upper side.

The medicinal liquid is not particularly limited, and may be, for example, a medicine that would be dangerous if a medical worker were to touch it by mistake, such as a carcinostatic, an immunosuppressor, etc. Other examples of medical liquids include sedatives, intravenous anesthetics, anesthetic analgesics, local anesthetics, antidepolarizing muscle relaxants, vasopressors, depressors, coronary vasodilators, diuretics, antiarrhythmics, bronchodilators, styptics, vitamin preparations, antibiotic drugs, lipid emulsions, etc. Incidentally, in the present embodiment, the medicinal liquid L is preliminarily stored in the prefilled syringe 80, and is obtained by transferring the medicinal liquid from the prefilled syringe 80 into an empty infusion bag 20. However, the method of obtaining the medicinal liquid L is not limited to this method. For example, another method may be used in which a medicinal liquid L having a comparatively high concentration is stored in the prefilled syringe 80, and the medicinal liquid L is diluted by transferring it from the prefilled syringe 80 into an infusion bag 20 filled with a diluting liquid.

Further, a method may be used in which, for example, a first liquid containing a component for producing a medical liquid L is stored in the prefilled syringe 80, and a second liquid containing a another component for producing the medical liquid L when mixed with the first liquid is stored in the infusion bag 20. The first liquid is transferred from the prefilled syringe 80 into the infusion bag 20 in order to mix the first liquid with the second liquid, thereby obtaining the medicinal liquid L.

Next, a method of operating the infusion tube set 1 (connector 2A) will be described below. Incidentally, although in the present embodiment, a case is described as an example in which two infusion tube sets 1 are used, the invention is not limited by this feature. For example, one infusion tube set 1 or three or more infusion tube sets 1 may also be used.

[A1]

As shown in FIG. 2, the infusion system 100 and the infusion tube sets 1 are prepared. In addition thereto, the infusion bags 20 and the prefilled syringe 80 are prepared. Next, an operation of the first one of the infusion tube sets 1 will be described below, it being understood that the second one of the infusion tube sets 1 is operated in the same manner.

Herein, a description will be made taking as an example a case in which the infusion system 100 is used as a main line (main route) for dosing a patient with a medicinal liquid L, namely, as a line in which an infusion that serves as a base liquid or the like is allowed to flow, whereas each infusion tube set 1 is used as an auxiliary line (auxiliary route) in which a medicinal liquid L that would be dangerous if touched by a medical worker, such as a carcinostatic or an immunosupressor, is allowed to flow. Further, an indwelling needle is preliminarily set indwelling in a patient's blood vessel (for example, a peripheral vein or the like).

[A2]

The connector 117 of the infusion system 100 is connected to the indwelling needle set indwelling in the patient's blood vessel.

[A3]

The infusion system 100 is primed by opening the clamp 106 in the infusion system 100.

[A4]

By operating the roller forceps 116 in the infusion system 100, the flow rate (administration rate) of the infusion M in the infusion system 100 is adjusted to a prescribed flow rate (prescribed administration rate), and the infusion M is administered.

[A5]

When the infusion tube set 1 (the liquid discharge port 23 of the connector 2A) is connected to the infusion system 100 (the tubular section 901 of the connector 90) for use in administering an antibiotic drug or the like at a predetermined time interval depending on the patient's condition, first, the bag-side connector 50 of the infusion tube set 1 is connected to the infusion bag 20 (see FIG. 2). Incidentally, the infusion bag 20 may be in empty or preliminarily filled with physiological saline or the like.

[A6]

The prefilled syringe 80 is connected to the syringe connection section 504 of the bag-side connector 50 that is connected to the infusion bag 20, and a plunger (not shown) of the prefilled syringe 80 is pushed. This results in the medicinal liquid L being transported from the prefilled syringe 80 into the infusion bag 20 through the bag-side connector 50.

[A7]

The clamp 40 in the infusion tube set 1 is opened, and the medicinal liquid L in the infusion bag 20 is allowed to flow, whereby the infusion tube set 1 is primed. Thus, in the infusion tube set 1, in a condition where the infusion tube set 1 is connected to the infusion bag 20, supply and discharge of the medicinal liquid L can be applied to the infusion bag 20. This makes it possible to omit operations of inserting and withdrawing the bag-side connector 50, for example, each time that supply and discharge of the medicinal liquid L is carried out by the infusion bag 20. Accordingly, good operability is secured.

Further, in this instance, the connector 2A is in a condition whereby the cap 10 is attached to the liquid discharge port 23, and the opening section 232 of the liquid discharge port 23 is sealed. In addition, the connector 2A is placed in the initial condition, in which the first flow path 221 of the inlet port 22 and the third flow path of the gas discharge port 25 communicate with each other through the changeover flow paths (flow paths 45 and 46) of the cock 4.

When the medicinal liquid L in the infusion bag 20 flows in this condition, the medicinal liquid L passes sequentially through the bag-side connector 50 and the tube 30, so as to flow into the first flow path 221 of the inlet port 22 of the connector 2A (see FIG. 5). In this instance, in the connector 2A, air G in the first flow path 221 is discharged through the third flow path 251 of the gas discharge port 25, as a result of the medicinal liquid L having flowed into the first flow path 221. In addition, attendant on discharge of the air G, the inside of the first flow path 221, as well as the inside of the flow paths 44 to 46 of the cock 4 and the inside of the third flow path 251, are gradually filled with the medicinal liquid L. Eventually, these flow paths become completely filled with the medicinal liquid L, and flow of the medicinal liquid L is temporarily stopped. Further, in this instance, the color change section 28 exhibits a change in color, whereby it can be visually confirmed that the inside of the first flow path 221 as well as the inside of the flow paths 44 to 46 of the cock 4 and the third flow path 251 have become completely filled with the medicinal liquid L (flow of the medicinal liquid L has stopped). In addition, the second flow path 231 of the liquid discharge port 23 is filled with air G, since the second flow path 231 communicates neither with the first flow path nor with the third flow path.

[A8]

After the change in color of the color change section 28 is confirmed, the tube 30 of the infusion tube set 1 is sealed by the clamp 40.

[A9]

The cap 10 is detached from the liquid discharge port 23 of the connector 2A, whereby the sealed state of the opening section 232 of the liquid discharge port 23 is released (see FIG. 6).

[A10]

The liquid discharge port 23 of the connector 2A and the tubular section 901 of the connector 90 are connected to each other (see FIG. 7). When this connection is made, as mentioned above, the second flow path 231 is filled with air G (i.e., is in an empty state). In other words, the medicinal liquid L has not yet flowed into the second flow path 231, and therefore, the medicinal liquid L in the connector 2A (the first flow path 221) is securely prevented from leaking or scattering to the exterior from the second flow path 231. This ensures that the connector 2A of the infusion tube set 1 and the connector 90 of the infusion system 100 can be connected to each other in a stable fashion (smoothly).

[A11]

The lever 43 of the cock 4 of the connector 2A is gripped, and the cock 4 is rotated counterclockwise by 90°, as shown in FIG. 8. This results in the gas discharge port 25 being closed, and the first flow path 221 of the inlet port 22 and the second flow path 231 of the liquid discharge port 23 being brought into communication with each other.

[A12]

The clamp 40 on the tube 30 of the infusion tube set 1 is opened again. This results in a resumption of flow of the medicinal liquid L, whereby the medicinal liquid L flows from the infusion tube set 1 into the infusion system 100. Then, the medicinal liquid L, having flowed into the infusion system 100, is administered to the patient. Thus, in the connector 2A, after completion of the connection between the connector 2A of the infusion tube set 1 and the connector 90 of the infusion system 100, flow of the medicinal liquid L is resumed speedily and assuredly, whereby administration of the medicinal liquid L can be performed. In this case, the drip tube 115 can reserve air G that has flowed into the drip tube 115 together with the medicinal liquid L, whereby such air G can be prevented from flowing downstream.

Incidentally, although in the present embodiment the infusion tube set 1 is equipped with the clamp 40 (see FIG. 2), the invention is not limited by this feature, and the clamp 40 may be omitted.

Second Embodiment

Figure 10:
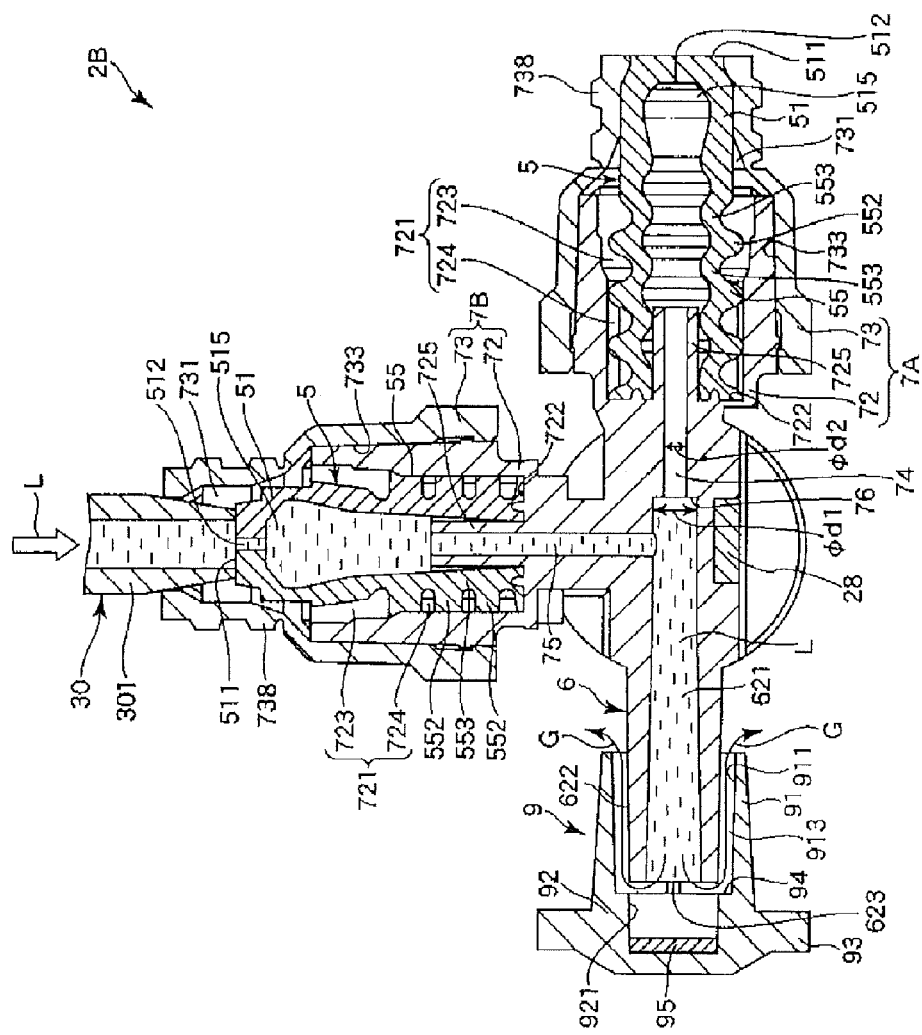
FIG. 10 is a view (a longitudinal sectional view) for sequentially illustrating an operation process of a connector (second embodiment) according to the present invention.
Figure 11:
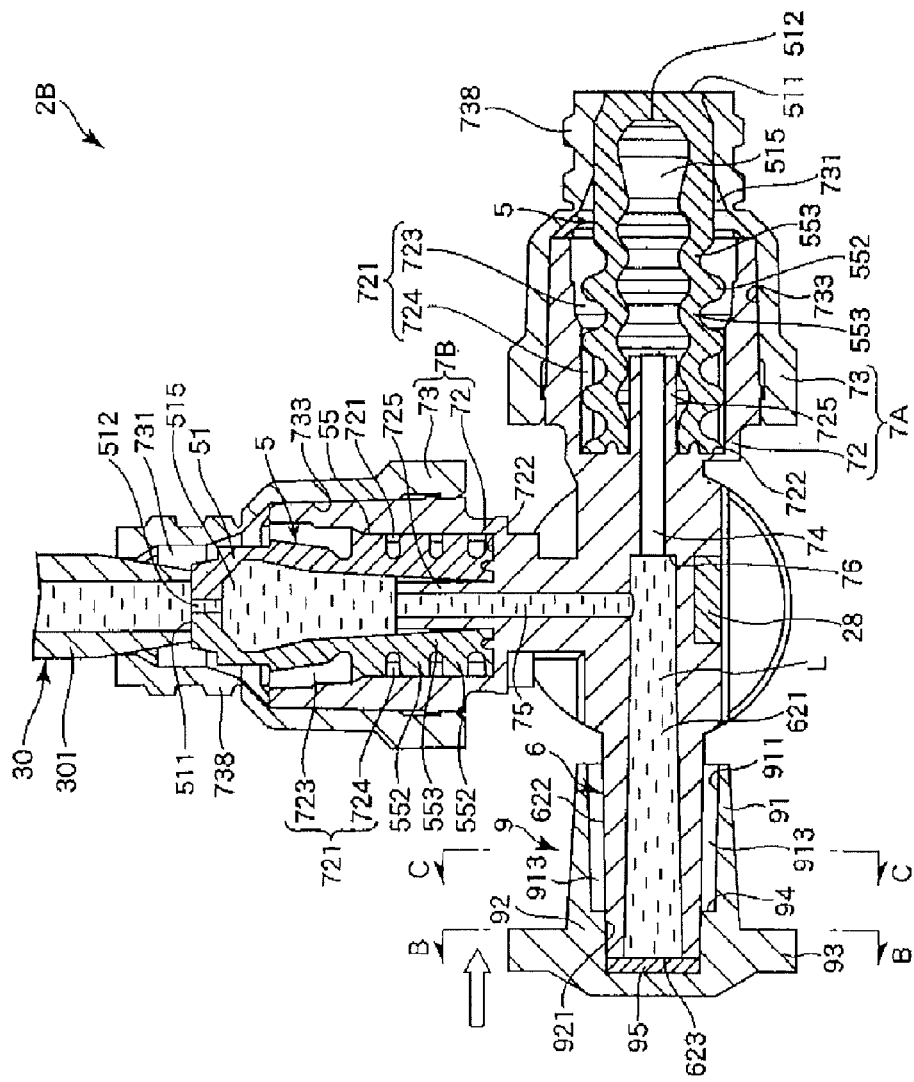
FIG. 11 is a view (a longitudinal sectional view) for sequentially illustrating the operation process of the connector (second embodiment) according to the present invention.
Figure 12:
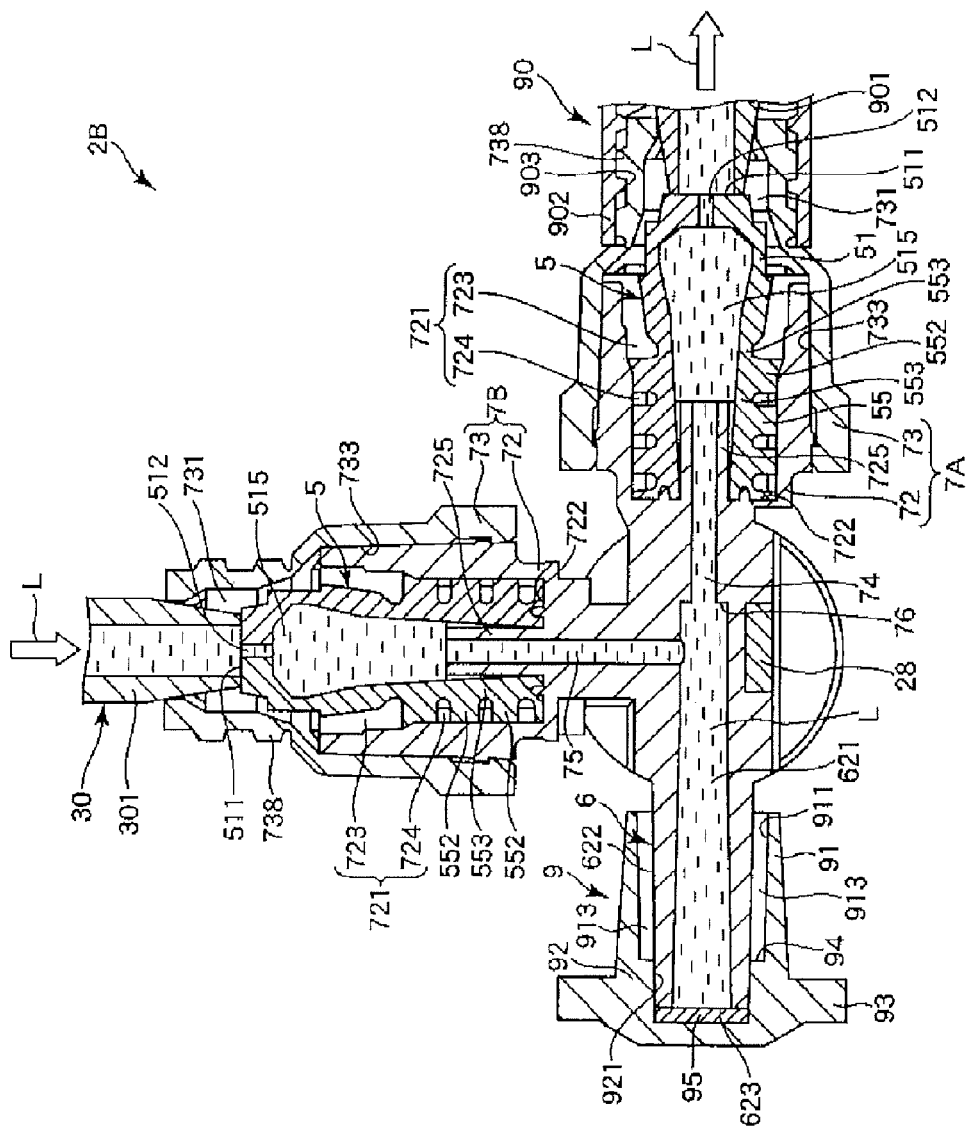
FIG. 12 is a view (a longitudinal sectional view) for sequentially illustrating the operation process of the connector (second embodiment) according to the present invention.
Figure 13:
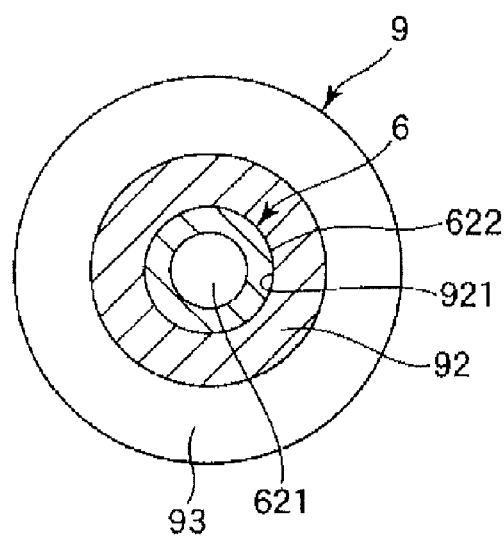
FIG. 13 is a sectional view taken alone line B-B of FIG. 11.
Figure 14:
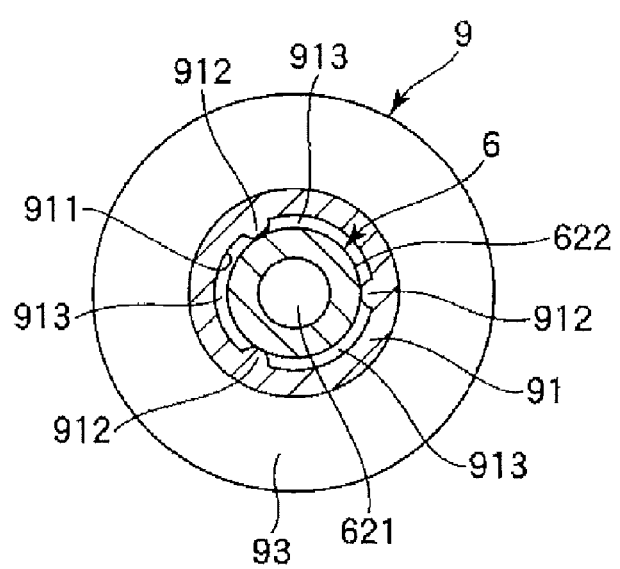
FIG. 14 is a sectional view taken along line C-C of FIG. 11.

FIGS. 10 to 12 are views (longitudinal sectional views) for sequentially illustrating an operation process of the connector (second embodiment) according to the present invention, FIG. 13 is a sectional view taken along line B-B of FIG. 11, and FIG. 14 is a sectional view taken along line C-C of FIG. 11. Incidentally, in the following, for facilitating description, the left side in FIGS. 10 to 12 will be referred to as "left" or "left side," the right side in the figures will be referred to as "right" or "right side," the upper side in the figures will be referred to as "upper" or "upper side," and the lower side in the figures will be referred to as "lower" or "lower side."

Next, referring to the aforementioned figures, a second embodiment of the connector and the infusion tube set according to the present invention will be described below. The following description shall be centered on differences from the above-described embodiment, and descriptions of the same items, which have already been discussed above, will be omitted.

This embodiment is the same as the above-described first embodiment, except for certain differences in the configuration (overall shape) of the connector.

A connector 2B shown in FIGS. 10 to 12 has three tubular ports. Among the three ports, two of the ports project in opposite directions. Hereinafter, concerning the two ports, the port located on the right side in FIG. 10 (also in FIGS. 11 and 12) will be referred to as a "liquid discharge port 7A" for discharging a medicinal liquid L, and the port located on the left side will be referred to as a "gas discharge port 6 (gas discharge means)" for discharging air G. In addition, the remaining one port projects in a direction (upward direction in FIG. 10) that is orthogonal to the liquid discharge port 7A and the gas discharge port 6. Hereinafter, the third port will be referred to as an "inlet port 7B" through which the medicinal liquid L is poured. Thus, in the connector 2B, the liquid discharge port 7A and the gas discharge port 6 are located (i.e., project) on opposite sides, with the inlet port 7B being located therebetween. The three ports are formed so as to be T-shaped as a whole.

In addition, the connector 2B additionally includes valve bodies 5 (blocking means), which are housed respectively in the liquid discharge port 7A and the inlet port 7B, and a cap 9 attached to the gas discharge port 6.

The liquid discharge port 7A is a part to which the connector 90 is connected, and into which the tubular section 901 of the connector 90 is inserted when such a connection is made (see FIG. 12). The configuration of the liquid discharge port 7A is substantially the same as the configuration of the inlet port 7B. In the following, therefore, description of the inlet port 7B will be omitted, and the liquid discharge port 7A will be described representatively.

As shown in FIG. 10 (also in FIGS. 11 and 12), the liquid discharge port 7A has a port body section 72 and a cover section 73.

The port body section 72 is formed therein with a valve body placing part 721. The valve body placing part 721 may be divided into a second inner cavity part (inner cavity part) 723 and a third inner cavity part (inner cavity part) 724, which is located on the side of the gas discharge port 6 relative to the second inner cavity part 723, and which is smaller in inside diameter than the second inner cavity part 723. In addition, the inside diameter of the third inner cavity part 724 preferably is slightly greater than the maximum outside diameter of a trunk part 55 of the valve body 5, to be described later.

Further, an inside projection 725, which is composed of a tubular body, is provided at a central portion of the bottom surface 722 of the port body section 72. When the valve body 5 begins to be pressed as shown in FIG. 12, the inside of the valve body 5 is supported by the inside projection 725, whereby buckling of the valve body 5 (bending of the valve body 5 into a dogleg shape) can be prevented. In addition, when the medicinal liquid L passes into the connector 2B, the medicinal liquid L can be prevented from stagnating.

The cover section 73 is provided with a space (inner cavity part) for storing the valve body 5 therein. The cover section 73 is connected (mounted) to the port body section 72 (valve body placing part 721).

The cover section 73 is provided therein with a first inner cavity part 731, in which a head part 51 of the valve body 5, to be described later, can be inserted, and a fitting part 733, which communicates with the first inner cavity part 731 and is larger in diameter than the first inner cavity part 731.

The first inner cavity part 731 is formed such that the shape thereof corresponds to the outer shape of the head part 51 of the valve body 5.

In addition, the fitting part 733 is fitted onto an outer peripheral portion of the port body section 72. This ensures that the cover section 73 and the port body section 72 are coupled to each other in a liquid-tight manner, so that the medicinal liquid L in the connector 2B can be prevented from leaking through the gap between the cover section 73 and the port body section 72. Further, when the cover section 73 and the port body section 72 are coupled to each other, the first inner cavity part 731 and the second inner cavity part 723 communicate with each other, and the valve body 5 can be placed (accommodated) in the space formed by the first inner cavity part 731, the second inner cavity part 723, and the third inner cavity part 724.

An outer peripheral portion of the cover section 73 is formed with a male screw part 738. In the liquid discharge port 7A, the male screw part 738 is screw-engaged with a female screw part 903, which is formed at an inner peripheral portion of a tubular lock part 902 disposed concentrically with the tubular section 901 of the connector 90 (see FIG. 12).

In the liquid discharge port 7A having such a configuration, the inside space (inner cavity part) functions as a flow path (second flow path 74) through which the medicinal liquid L can pass. In addition, in the inlet port 7B, the inside space (inner cavity part) functions as a flow path (first flow path 75) through which the medicinal liquid L can pass, similar to the liquid discharge port 7A. The first flow path 75 and the second flow path 74 are orthogonal to each other, and communicate with each other.

Further, in the vicinity of a boundary part between the first flow path 75 and the second flow path 74, the inside diameter ϕd2 of the second flow path 74 is smaller than the inside diameter ϕd1 of the first flow path 75 (see FIG. 10). Therefore, a stepped section 76 is formed at the boundary part. In addition, the portion of the first flow path 75, where the inside diameter is ϕd1, is formed continuously with the third flow path 621 of the gas discharge port 6. With the flow paths configured in this manner, when the medicinal liquid L flows into the first flow path 75, the medicinal liquid L flows preferentially into the third flow path 621, due to a synergistic effect in which the flow toward the second flow path 74 side is temporarily inhibited by the stepped section 76, the inside diameter of the third flow path 621 is greater than the inside diameter of the second flow path 74, and the third flow path 621 extends in a direction opposite to the second flow path 74 (see FIG. 10). Therefore, in the connector 2B, the stepped section 76 forms a part that functions as a blocking means in which, upon pouring of the medicinal liquid L into the first flow path 75, flow of the medicinal liquid L into the second flow path 74 is temporarily stopped before the medicinal liquid L reaches the second flow path 74.

Further, the stepped section 76 or the vicinity thereof may be made hydrophobic. This ensures that further flow of the medicinal liquid L, which has already flowed into the first flow path 75 toward the side of the second flow path 74, can be temporarily stopped in an assured manner. The method for rendering the stepped section 76 hydrophobic is not particularly limited. Examples of such methods include a method in which the stepped section 76 is subjected to a hydrophobicity-imparting treatment (water repellency imparting treatment). Examples of the hydrophobicity-imparting treatment include formation of a coating film composed of a water-repellent material (hydrophobic material), for example, a fluororesin such as polytetrafluoroethylene (PTFE) and ethylene-tetrafluoroethylene copolymer.

As shown in FIG. 10, the valve bodies 5 are housed (fixed) respectively in the liquid discharge port 7A (second flow path 74) and in the inlet port 7B (first flow path 75).

The valve bodies 5 are formed from an elastic material. Examples of suitable elastic materials include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., and various thermoplastic elastomers based on styrene, polyolefin, polyvinyl chloride, polyurethane, polyester, polyamide, polybutadiene, trans-polyisoprene, fluororubber, chlorinated polyethylene or the like. One of these materials, or two or more of such materials in mixture, may be used. Through use of such an elastic material, a top face 511 of the valve body 5 can have an appropriate elasticity imparted thereto. This ensures that when a tubular body (for example, a distal portion 301 of the tube 30, or the tubular section 901 of the connector 90) is connected to the liquid discharge port 7A (or to the inlet port 7B), an end face of the tubular body and the top face 511 can come into contact with each other in a liquid-tight manner.

As shown in FIG. 10, the valve body 5 has a tubular trunk part 55, and a head part 51 formed integrally with one end portion of the trunk part 55.

The head part 51 has a bottomed tubular shape, and is formed with an inner cavity part 515 that permits the medicinal liquid L to pass therethrough, and a slit (opening/closing part) 512 extending from the flat top face 511 to reach the inner cavity part 515. The slit 512 is substantially formed in the shape of a straight line segment. Since the slit 512 is simple in shape, when the top face 511 (the vicinity of the slit 512) is pressed, the top face 511 is deformed, so that the slit 512 can be opened easily (assuredly). In addition, when pressing is released, the top face 511 is restored to its original shape, whereby the slit 512 is securely closed. Thus, the valve body 5 has a self-closing property.

Further, by operation of the slit 512, the opening section (second flow path 74) of the liquid discharge port 7A can be sealed (see FIGS. 10 and 11) and unsealed (see FIG. 13) easily and assuredly.

In addition, since the top face 511 is flat, when the above-mentioned tubular body is connected, the top face 511 (slit 512) can preliminarily be disinfected easily.

Further, when pressure is not exerted thereon, the head part 51 is inserted into the first inner cavity part 731 of the cover section 73, and the slit 512 is closed.

The trunk part 55 is composed of a bellows-like tubular body. More specifically, the trunk part 55 has a bellows-like shape having an outer shape in which large-diameter ring portions 552 and small-diameter ring portions 553 are alternately arrayed along the axial direction. The trunk part 55 thus shaped functions as a deforming part (biasing means) for biasing the valve body 5 away from the side of the trunk part 55 toward the side of the head part 51 (in the direction in which the head part 51 is inserted into the first inner cavity part 731 of the cover section 73).

Since the trunk part 55 functions as a deforming part, it is unnecessary to provide the connector 2B separately with a component part that constitutes the biasing means. This contributes to a reduction in the number of component parts and simplifies the structure thereof.

In addition, although the trunk part 55 provides most of the restoring force for restoring the valve body 5 from the side of the trunk part 55 to the side of the head part 51, the head part 51 may provide a portion of the restoring force as well.

When the medicinal liquid L is poured into the first flow path 75 in a condition where the slit 512 of the valve body 5 is closed, as shown in FIG. 10, air G is confined in the second flow path 74. When the medicinal liquid L is further poured into the first flow path 75 such that the first flow path 75 is filled with the medicinal liquid L, the internal pressure in the second flow path 74 is raised to such an extent that inflow of the medicinal liquid L into the second flow path 74 is inhibited. This ensures that flow of the medicinal liquid L is temporarily stopped (see FIG. 11) before the medicinal liquid L reaches the second flow path 74. When the connector 90 is connected to the liquid discharge port 7A, as shown in FIG. 12, the head part 51 (slit 512) of the valve body 5 is pressed by the tubular section 901 of the connector 90 and is deformed thereby, whereby the slit 512 is placed in an open state. As a result, the second flow path 74 is opened, and the medicinal liquid L is permitted to be transported into the connector 90 through the liquid discharge port 7A (second flow path 74).

The gas discharge port 6 is disposed on a side opposite to the liquid discharge port 7A. The gas discharge port 6 forms a part through which air G in the first flow path 75 is discharged when the medicinal liquid L is poured into the first flow path 75. The gas discharge port 6 is tubular in shape, and the inner cavity thereof functions as the third flow path 621 for permitting the medicinal liquid L to pass therethrough. Further, one end portion (the left side in FIG. 10) of the third flow path 621 is open, whereas the other end portion (the right side in FIG. 10) of the third flow path 621 communicates with the second flow path 74 and the first flow path 75.

In addition, the gas discharge port 6 has a luer taper section (taper section) 622, the outside diameter of which gradually decreases toward the side of the opening section 623 of the third flow path 621.

A cap 9 is mounted onto the gas discharge port 6. The cap 9 has a bottomed tubular shape as a whole, and can be divided into a mounting section 91 for being mounted to an outer peripheral portion (luer taper section 622) of the gas discharge port 6, a sealing section 92 capable of sealing the opening section 623 of the third flow path 621 in a liquid-tight manner, and an operating section 93 for performing an operation to move the cap 9.

The cap 9 is formed with a stepped section 94 at which the inside diameter thereof is changed. The right side of the stepped section 94 forms the mounting section 91, and the left side of the stepped section 94 forms the sealing section 92.

The mounting section 91 has a plurality of (in the configuration shown in FIG. 14, three) ribs (linear projections) 912 formed on the inner peripheral portion 911 thereof. The ribs 912 are formed along the axial direction of the mounting section 91, and are in contact with the luer taper section 622 of the gas discharge port 6. This ensures that the cap 9 is supported relative to the gas discharge port 6, so that the cap 9 can be moved stably along the axial direction.

As shown in FIG. 14, the ribs 912 are laid out at regular angular intervals around the center axis of the mounting section 91. Consequently, the cap 9 is stably supported relative to the gas discharge port 6, and the cap 9 can easily be moved.

In addition, gaps are formed between the adjacent ribs 912. Each of such gaps functions as a vent path 913 through which gas passes (see FIG. 10). A total of the cross-sectional areas of the gaps is preferably not less than 20%, and more preferably is 35 to 98%, based on the total cross-sectional area of the opening section 623.

The sealing section 92 is reduced in inside diameter as compared with the mounting section 91. This ensures that an inner peripheral portion 921 of the sealing section 92 can be fitted to the luer taper section 622 of the gas discharge port 6 (see FIG. 13), so that the opening section 623 of the third flow path 621 can be securely sealed, and the third flow path 621 and the vent path 913 are shut (closed) (see FIGS. 11 and 12). The position of the sealing section 92 in this instance is referred to as a "sealing position." Further, when the gap 9 (sealing section 92) is moved to the left from the sealing position, the inner peripheral portion 921 of the sealing section 92 and the luer taper section 622 of the gas discharge port 6 are spaced from each other, so that the opening section 623 of the third flow path 621 becomes unsealed (see FIG. 10). The position of the sealing section 92 in this instance is referred to as an "unsealing position." Before the connector 2B is used, the cap 9 is disposed in the unsealing position.

Incidentally, a packing (seal member) 95 formed from an elastic material (e.g., rubber material) may be disposed at a bottom portion of the sealing section 92. This ensures that, in the sealing position, the packing 95 closes the opening section 623 of the third flow path 621, so that the opening section 623 of the third flow path 621 can be sealed more securely. The packing 95 may be disposed at the inner peripheral portion 921 of the sealing section 92, in which case, the packing may be in the shape of an O-ring.

A flange is formed to project on an outer peripheral portion of the sealing section 92. The flange is a plate-shaped part, which is enlarged in diameter as compared with the outside diameter of the outer peripheral portion of the sealing section 92, and the flange functions as the operating section 93. When the sealing section 92 is moved from the sealing position to the unsealing position, or from the unsealing position to the sealing position, the operation can be performed by placing a finger on the operating section 93.

Next, a method of operating the connector 2B will be described below.

[B1]

Priming is conducted in the condition shown in FIG. 10, namely, in a condition in which the cap 9 is in the unsealing position, and the valve body 5 shown on the right side in the figure is closed. In this instance, the medicinal liquid L first passes through the tube 30 and flows into the first flow path 75 of the inlet port 7B. As a result, air G in the first flow path 75 is discharged by sequentially passing through the third flow path 621 of the gas discharge port 6 and the vent path 913. Attendant on discharge of the air G, the inside of the first flow path 75 and the inside of the third flow path 621 are gradually filled with the medicinal liquid L. Eventually, the flow paths become completely filled with the medicinal liquid L. In this instance, the color change section 28 exhibits a change in color as mentioned above, so that it can be visually confirmed that the inside of the first flow path 75 and the inside of the third flow path 621 have been completely filled with the medicinal liquid L.

In addition, as mentioned above, because the medicinal liquid L does not flow into the second flow path 74 of the liquid discharge port 7A, the second flow path 74 remains filled with air G.

[B2]

After the color change of the color change section 28 has been confirmed, the cap 9 is operated in the direction of arrow in FIG. 11, to place the cap 9 in the sealing position. Consequently, the opening section 623 of the third flow path 621 is sealed, and the medicinal liquid L cannot go anywhere, so that flow of the medicinal liquid L is momentarily stopped (see FIG. 11).

[B3]

As shown in FIG. 12, the liquid discharge port 7A of the connector 2B and the tubular section 901 of the connector 90 are connected to each other. In this instance, as mentioned above, the valve body 5 is deformed toward the right as shown in FIG. 12, and the slit 512 is placed in the open state. In other words, the opening section of the liquid discharge port 7A becomes unsealed. In addition, when this connection is made, as mentioned above, the inside of the second flow path 74 is filled with air G, so that the medicinal liquid L in the connector 2B is securely prevented from leaking or scattering to the exterior from the second flow path 74. Consequently, connection between the connectors can be carried out safely (smoothly).

Then, when the connectors are connected to each other (when the valve body 5 on the right side in FIG. 12 is placed in an open state), a place is provided to which the medicinal liquid L in the connector 2B can go. More specifically, the medicinal liquid L is permitted to flow into the second flow path 74. Consequently, flow of the medicinal liquid L is resumed, and the medicinal liquid L flows into the connector 90 through the second flow path 74.

Third Embodiment

FIGS. 15 to 20 are views (longitudinal sectional views) for sequentially illustrating an operation process of the connector (third embodiment) according to the present invention. Incidentally, in the following, for facilitating description, the right side in FIGS. 15 to 20 will be referred to as "proximal (end)," and the left side as "distal (end)."

Next, referring to these figures, a third embodiment of the connector according to the present invention will be described. The following description will be centered on differences from the above-described embodiments, and descriptions of the same items, which have already been described above, will be omitted.

This embodiment is the same as the aforementioned first embodiment, except for certain differences in the configuration of the blocking means.

Figure 16:
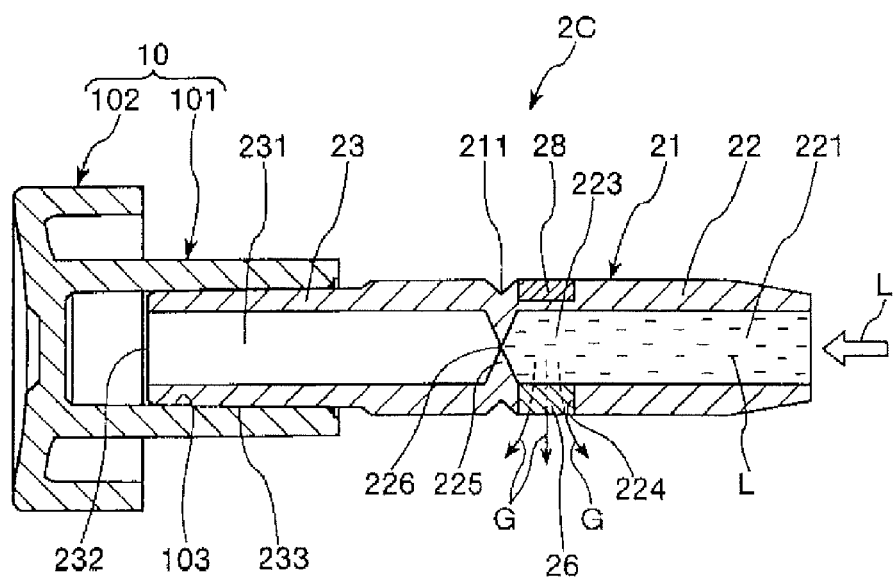
FIG. 16 is a view (a longitudinal sectional view) for sequentially illustrating the operation process of the connector (third embodiment) according to the present invention.

In a connector 2C shown in the figures, an inlet port 22 is formed with a through-hole 224 that penetrates through a wall portion thereof. The through-hole 224 is disposed in a distal portion 223 of a first flow path 221, and more specifically, in the vicinity of a boundary part between the first flow path 221 and a second flow path 231. A filter member 26 is fitted (disposed) in the through-hole 224. As shown in FIG. 16, when a medicinal liquid L is poured into the first flow path 221 of the inlet port 22, air in the first flow path 221 is securely discharged through the filter member 26.

In addition, a rupture unsealing section (unsealing section) 225 is provided at a boundary part between the first flow path 221 and the second flow path 231. The rupture unsealing section 225 is plate-like in shape, and is formed so as to shut off the first flow path 221 and the second flow path 231 from each other. This ensures that, upon flow of the medicinal liquid L into the first flow path 221 of the inlet port 22, the medicinal liquid L is inhibited from reaching the second flow path 231 of the liquid discharge port 23, whereby flow of the medicinal liquid L is stopped (see FIGS. 16 to 18). Thus, the rupture unsealing section 225 functions as a blocking means.

Figure 19:
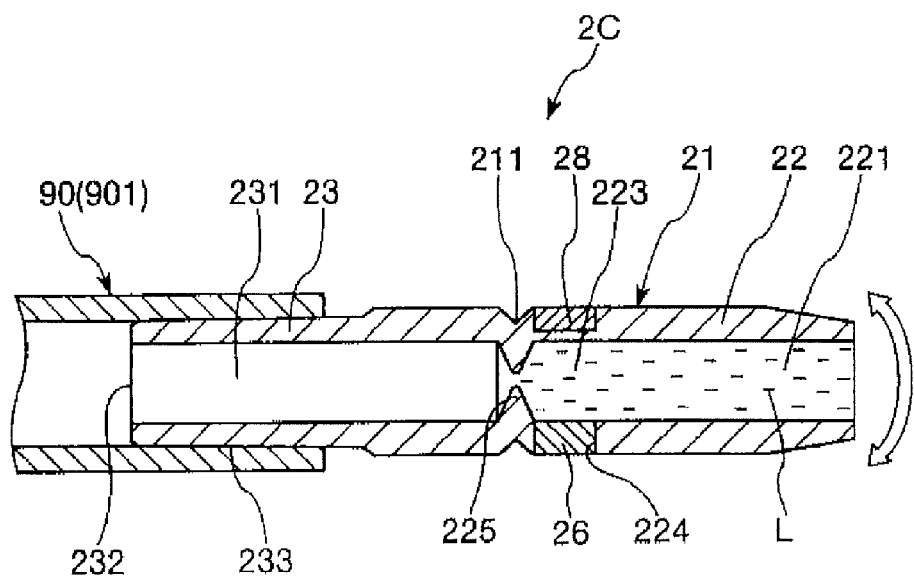
FIG. 19 is a view (a longitudinal sectional view) for sequentially illustrating the operation process of the connector (third embodiment) according to the present invention.
Figure 20:
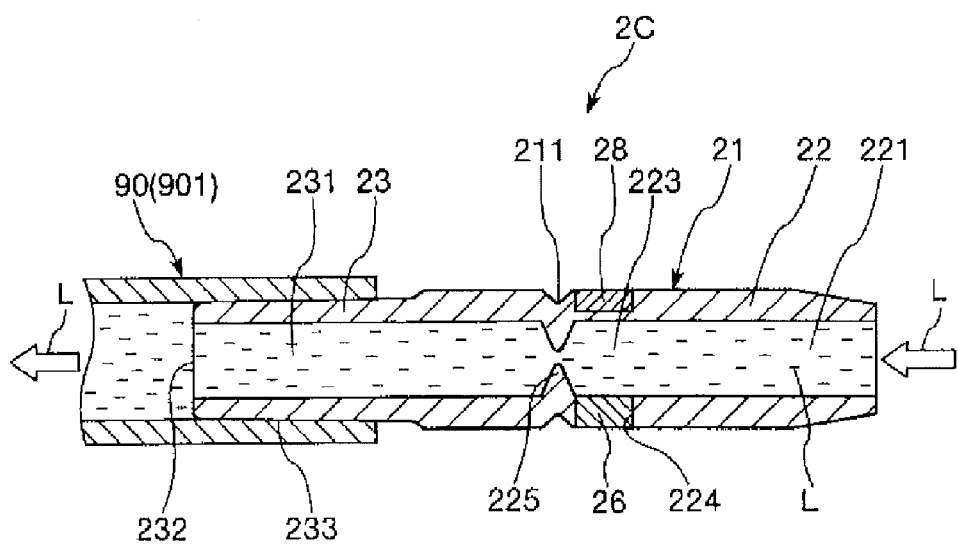
FIG. 20 is a view (a longitudinal sectional view) for sequentially illustrating the operation process of the connector (third embodiment) according to the present invention.

Further, the rupture unsealing section 225 is unsealed by rupturing the rupture unsealing section 225, thus causing the first flow path 221 and the second flow path 231 to communicate with each other (see FIG. 19). The rupture unsealing section 225 is thinner at a central portion 226 than at the edge portion (outer peripheral portion) thereof. This ensures that, when the inlet port 22 is displaced by being bent in the vertical direction in FIG. 19, such that a portion of the rupture unsealing section 225 of the connector body 21 forms a center of such bending, the central portion 226 of the rupture unsealing section 225 can be ruptured easily and assuredly.

In addition, an outer peripheral portion of the connector body 21 is formed with a neck-like part (reduced diameter part) 211 reduced in outside diameter, at a position corresponding to the rupture unsealing section 225. When the aforementioned bending operation is applied to the inlet port 22, the operation is facilitated, since the wall portion of the connector body 21 is reduced in thickness due to the presence of the neck-like part 211.

Next, a method of operating the connector 2C will be described below.

[C1]

Figure 15:
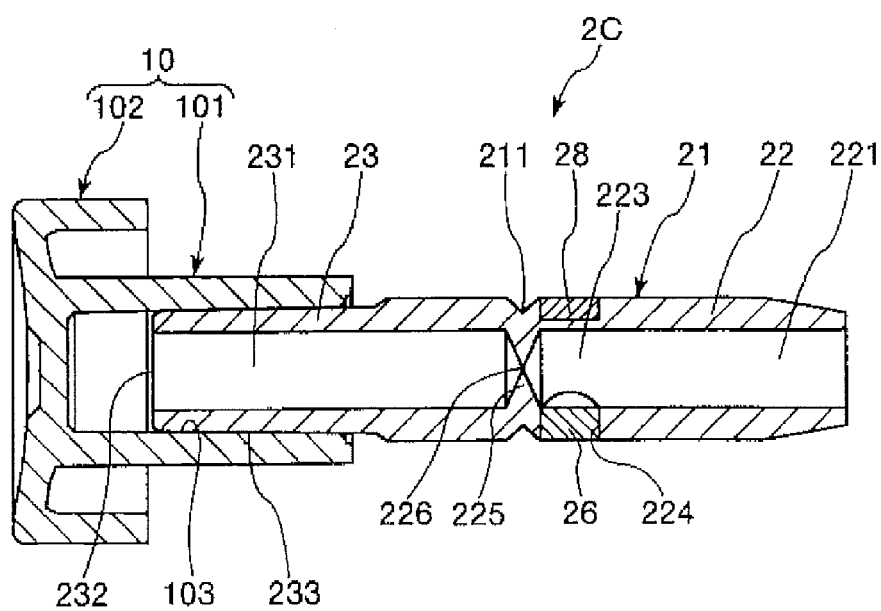
FIG. 15 is a view (a longitudinal sectional view) for sequentially illustrating an operation process of a connector (third embodiment) according to the present invention.

Starting from the condition shown in FIG. 15, namely, the condition in which a cap 10 is mounted to a liquid discharge port 23, thereby sealing the opening section 232 of the liquid discharge port 23, the medicinal liquid L is allowed to flow into the first flow path 221 of the inlet port 22 of the connector 2C, as shown in FIG. 16. In this instance, in the connector 22C, air G in the first flow path 221 is discharged through the filter member 26 as a result of the medicinal liquid L flowing into the first flow path 221. Further, attendant on discharge of the air G, the inside of the first flow path 221 gradually is filled with the medicinal liquid L. Eventually, the first flow path 221 becomes completely filled with the medicinal liquid L, and flow of the medicinal liquid L is momentarily stopped (see FIG. 17). In addition, at this time, as mentioned above, the color change section 28 exhibits a change in color, whereby it can be visually confirmed that the inside of the first flow path 221 has completely been filled with the medicinal liquid L, and that flow of the medicinal liquid L has been stopped. Further, the second flow path 231 of the liquid discharge port 23 is filled with air G, since the second flow path 231 does not communicate with the first flow path 221.

[C2]

Figure 17:
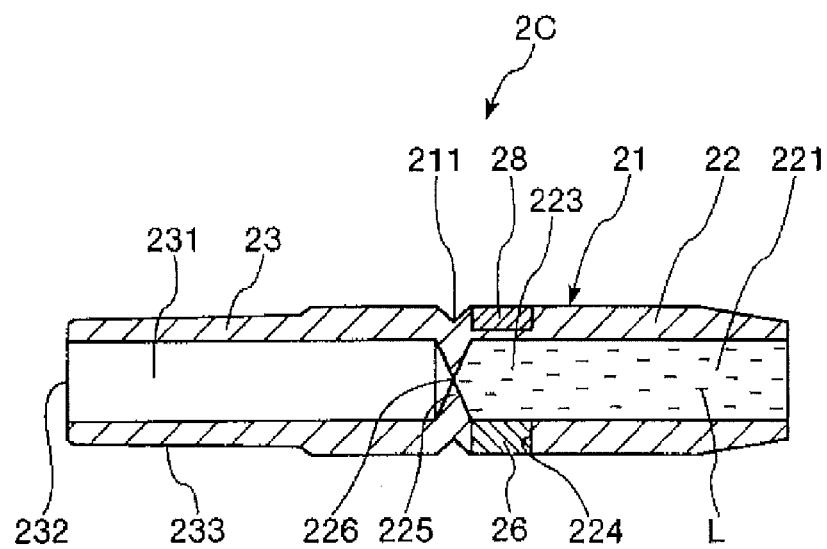
FIG. 17 is a view (a longitudinal sectional view) for sequentially illustrating the operation process of the connector (third embodiment) according to the present invention.

After the change in color of the color change section 28 has been confirmed, the cap 10 is detached from the liquid discharge port 23 of the connector 2C, thereby unsealing the opening section 232 of the liquid discharge port 23 (see FIG. 17).

[C3]

Figure 18:
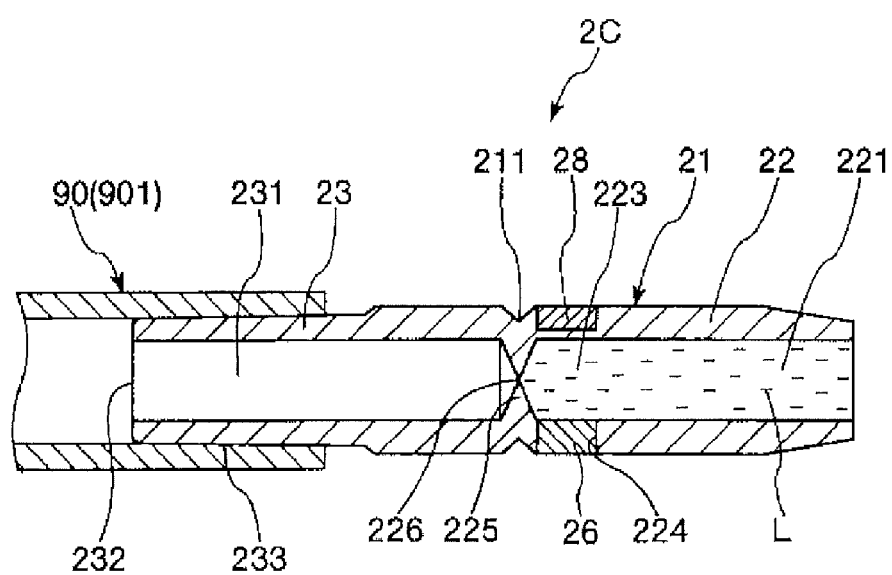
FIG. 18 is a view (a longitudinal sectional view) for sequentially illustrating the operation process of the connector (third embodiment) according to the present invention.

A tubular section 901 of a connector 90 is connected to the liquid discharge port 23 of the connector 2C (see FIG. 18). When this connection is made, as mentioned above, the inside of the second flow path 231 becomes filled with air G, so that the medicinal liquid L in the connector 2C (first flow path 221) is securely prevented from leaking or scattering to the exterior from the second flow path 231. Accordingly, the connection between the connector 2C and the connector 90 can be carried out safely.

[C4]

As shown in FIG. 19, the aforementioned bending operation is applied to the inlet port 22. As a result, the rupture unsealing section 225 is unsealed, so that the first flow path 221 of the inlet port 22 and the second flow path 231 of the liquid discharge port 23 come into communication with each other. Then, flow of the medicinal liquid L is resumed, and the medicinal liquid L flows from the connector 2C into the connector 90 (see FIG. 20).

Fourth Embodiment

FIGS. 21 to 24 are views (longitudinal sectional views) for sequentially illustrating an operation process of the connector (fourth embodiment) according to the present invention. Incidentally, in the following, for facilitating description, the right side in FIGS. 21 to 24 will be referred to as "proximal (end)," and the left side as "distal (end)."

Referring to the figures, a fourth embodiment of the connector according to the present invention will be described below. The following description shall be centered on differences from the above-described embodiments, and descriptions of the same items, which have already been described above, will be omitted.

This embodiment is the same as the above-described third embodiment, except for certain differences in the configuration of the blocking means.

The connector 2E shown in the figures is provided, at a boundary part between a first flow path 221 and a second flow path 231, with a tapered section 212. The inside diameter of the tapered section 212 gradually decreases toward the side of the second flow path 231.

Figure 22:
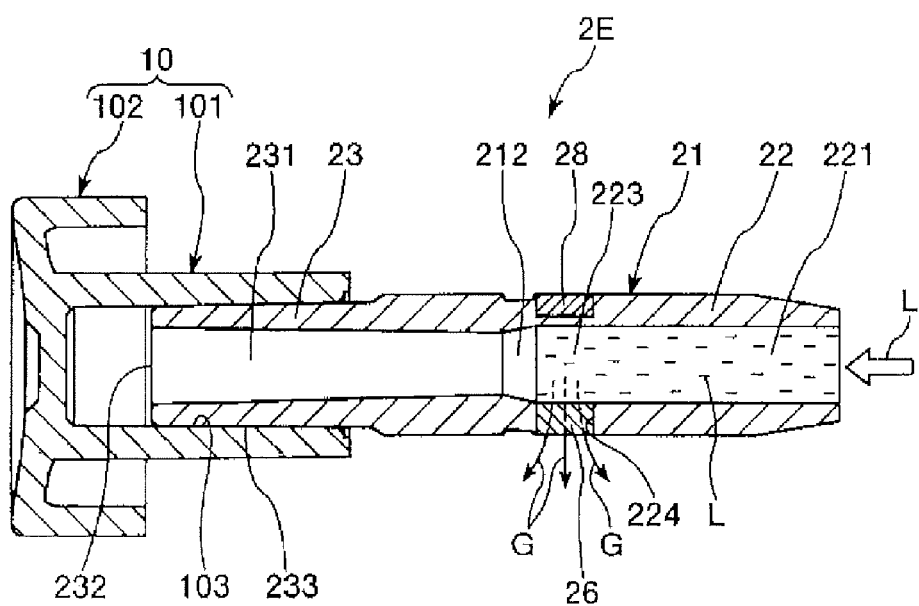
FIG. 22 is a view (a longitudinal sectional view) for sequentially illustrating the operation process of the connector (fourth embodiment) according to the present invention.

When a medicinal liquid L is poured into the first flow path 221, as shown in FIG. 22, air G gradually is confined in the second flow path 231, attendant on inflow of the medicinal liquid L. When the medicinal liquid L is further poured into the first flow path 75 and the inside of the first flow path 75 becomes filled with the medicinal liquid, the internal pressure in the second flow path 231 is raised to such an extent that inflow of the medicinal liquid L into the second flow path 74 is inhibited. As a result, before the medicinal liquid L reaches the second flow path 74, flow of the medicinal liquid L is momentarily stopped.

In addition, when the medicinal liquid L is poured into the first flow path 75, the medicinal liquid L is momentarily inhibited by the tapered section 212 from flowing toward the side of the second flow path 74.

Thus, in the connector 2E, the cap 10 and the tapered section 212 constitute a blocking means.

Incidentally, the tapered section 212 or the vicinity thereof may be made hydrophobic. This ensures that, having flowed into the first flow path 221, further flow of the medicinal liquid L toward the side of the second flow path 231 can be momentarily stopped more assuredly. The method of rendering the tapered section 212 hydrophobic is not particularly limited. Examples of such methods include a method in which the tapered section 212 is subjected to a hydrophobicity-imparting treatment (water repellency imparting treatment), similar to the stepped section 76.

A method of operating the connector 2E will be described.

[E1]

Figure 21:
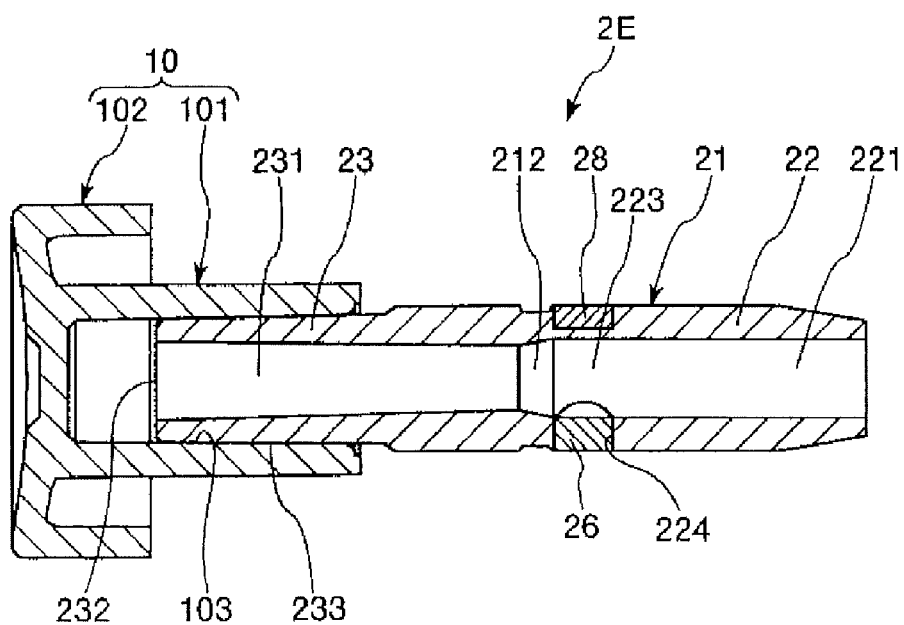
FIG. 21 is a view (a longitudinal sectional view) for sequentially illustrating an operation process of a connector (fourth embodiment) according to the present invention.

Starting from the condition shown in FIG. 21, namely, the condition in which the cap 10 is attached to the liquid discharge port 23 and the opening section 232 of the liquid discharge port 23 is sealed, the medicinal liquid L is allowed to flow into the first flow path 221 of the inlet port 22 of the connector 2E, as shown in FIG. 22. In this instance, in the connector 2E, air G in the first flow path 221 is discharged through the filter member 26 as a result of the medicinal liquid L having flowed into the first flow path 221 (see FIG. 22). In addition, attendant on discharge of the air G, the inside of the first flow path 221 gradually becomes filled with the medicinal liquid L. Then, as mentioned above, when the first flow path 221 is completely filled with the medicinal liquid L, flow of the medicinal liquid L is momentarily stopped (see FIG. 22). Further, in this instance, the color change section 28 exhibits a change in color, as mentioned above, whereby it can be visually confirmed that the inside of the first flow path 221 has been completely filled with the medicinal liquid L, and that flow of the medicinal liquid L has been stopped. In addition, since the medicinal liquid L has not yet entered therein, the second flow path 231 of the liquid discharge port 23 is filled with air G

[E2]

Figure 23:
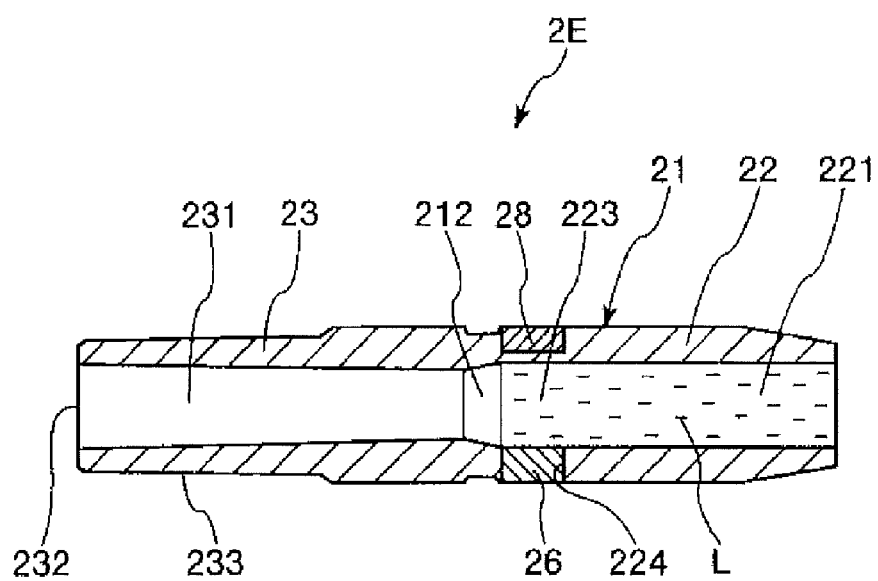
FIG. 23 is a view (a longitudinal sectional view) for sequentially illustrating the operation process of the connector (fourth embodiment) according to the present invention.

After the change in color of the color change section 28 has been confirmed, the tube 30 is sealed by the clamp 40, the cap 10 is detached from the liquid discharge port 23 of the connector 2E, and the opening section 232 of the liquid discharge port 23 is unsealed (see FIG. 23).

[E3]

Figure 24:
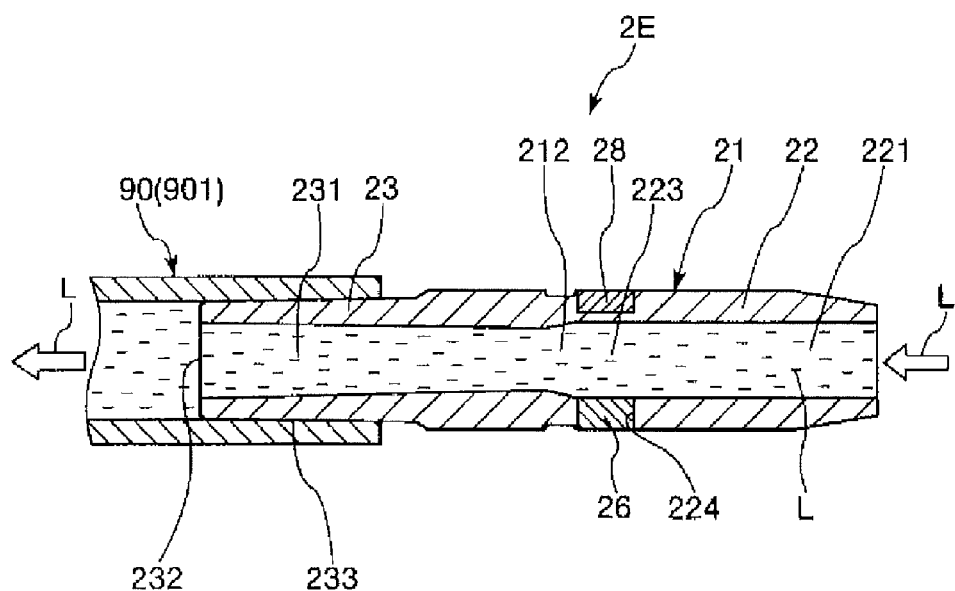
FIG. 24 is a view (a longitudinal sectional view) for sequentially illustrating the operation process of the connector (fourth embodiment) according to the present invention.

Immediately after the cap 10 has been detached, the tubular section 901 of the connector 90 is connected to the liquid discharge port 23 of the connector 2E (see FIG. 24). When this connection is made, as mentioned above, the inside of the second flow path 231 is filled with air G, so that the medicinal liquid L in the connector 2E (first flow path 221) is securely prevented from leaking or scattering to the exterior from the second flow path 231. Consequently, the connection between the connector 2E and the connector 90 can be carried out safely.

In this case, since a partition wall is not disposed between the medicinal liquid L and the second flow path 231, the length of the second flow path 231 preferably is not less than 0.1 mm and not greater than 20 mm. This ensures that adhesion of the medicinal liquid L to the cap 10 due to surface tension of the medicinal liquid L, and outward scattering of the medicinal liquid L, can be securely prevented.

In addition, after the connection has been made, the clamp 40 is opened, whereby flow of the medicinal liquid L is resumed, and the medicinal liquid L flows from the connector 2E into the connector 90 (see FIG. 24).

Fifth Embodiment

FIGS. 25 to 28 are views (longitudinal sectional views) for sequentially illustrating an operation process of the connector (fifth embodiment) according to the present invention. Incidentally, in the following descriptions, for facilitating explanation thereof, the right side in FIGS. 25 to 28 will be referred to as "proximal (end)," and the left side as "distal (end)."

Next, referring to the figures, a fifth embodiment of the connector according to the present invention will be described below. The following description shall be centered on differences from the above-described embodiments, and descriptions of the same items, which have already been described above, will be omitted.

This embodiment is the same as the above-described fourth embodiment, except for differences in the configuration of the seal member for sealing the opening section of the liquid discharge port in a liquid-tight (gas-tight) manner.

Figure 25:
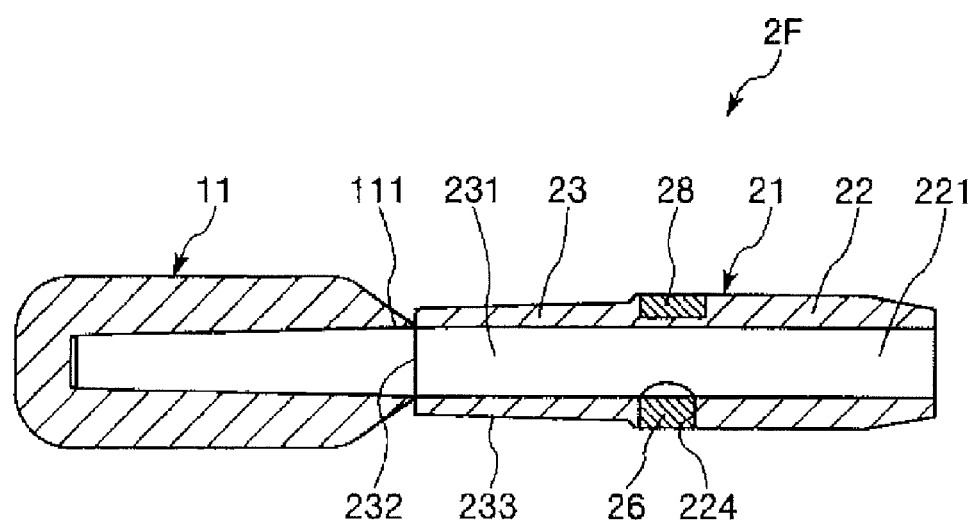
FIG. 25 is a view (a longitudinal sectional view) for sequentially illustrating an operation process of a connector (fifth embodiment) according to the present invention.
Figure 26:
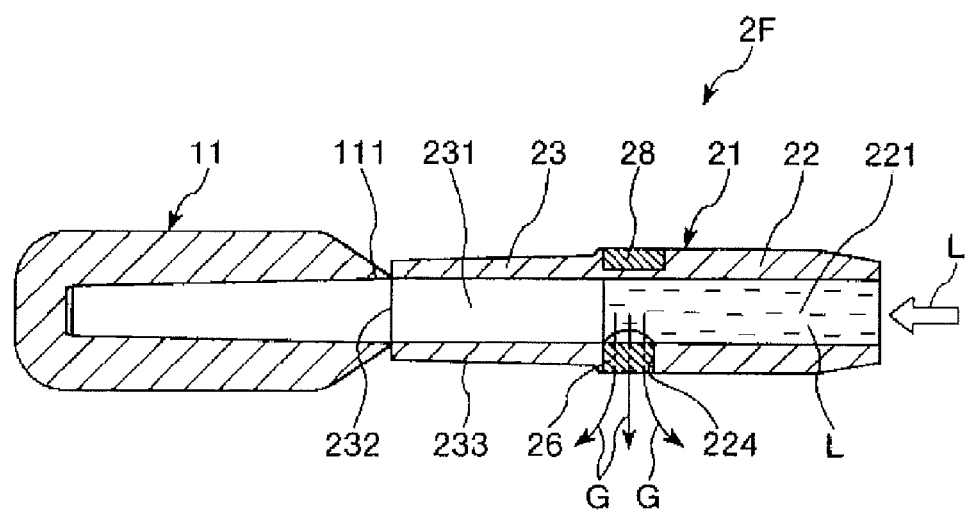
FIG. 26 is a view (a longitudinal sectional view) for sequentially illustrating the operation process of the connector (fifth embodiment) according to the present invention.

As shown in FIGS. 25 and 26, in the connector 2F, a click chip 11 is formed integrally at an opening section 232 of a liquid discharge port 23. The click chip 11 is configured such that the opening section 232 of the liquid discharge port 23 can be unsealed by rupturing the click chip 11 (see FIG. 27).

The click chip 11 is a tubular member, which is closed at a distal end thereof. A proximal portion 111 of the click chip 11, or a connection portion for connection with the opening section 232 of the liquid discharge port 23, is the smallest in terms of wall thickness. This ensures that, when the click chip 11 is ruptured, the rupturing operation can be carried out easily.

When the medicinal liquid L is poured into the first flow path 221, as shown in FIG. 26, air G is gradually confined in the second flow path 231 by action of the click chip 11, attendant on inflow of the medicinal liquid L. When the medicinal liquid L is further poured into the first flow path 75 such that the inside of the first flow path 75 becomes filled with the medicinal liquid L, the internal pressure in the second flow path 231 is raised to such an extent that inflow of the medicinal liquid L into the second flow path 74 is inhibited. This ensures that flow of the medicinal liquid L is momentarily stopped before the medicinal liquid L reaches the second flow path 74. Thus, in the connector 2F, the click chip 11 constitutes a blocking means.

A method of operating the connector 2F will be described.

[F1]

Starting from the condition shown in FIG. 25, namely, the condition in which the click chip 11 is not yet joined to (disposed on) the liquid discharge port 23, the medicinal liquid L is allowed to flow into the first flow path 221 of the inlet port 22 of the connector 2F, as shown in FIG. 26. In this instance, in the connector 2F, air G in the first flow path 221 is discharged through a filter member 26 as a result of the medicinal liquid L having flowed into the first flow path 221 (see FIG. 26). In addition, attendant on discharge of the air G, the inside of the first flow path 221 is gradually filled with the medicinal liquid L. Then, as mentioned above, when the first flow path 221 is completely filled with the medicinal liquid L, flow of the medicinal liquid L is momentarily stopped (see FIG. 26). Further, in this instance, the color change section 28 exhibits a change in color as discussed earlier, whereby it can be visually confirmed that the inside of the first flow path 221 has been completely filled with the medicinal liquid L, and that flow of the medicinal liquid L has been stopped. In addition, since the medicinal liquid L has not yet entered therein, the second flow path 231 of the liquid discharge port 23 remains filled up with air G.

[F2]

Figure 27:
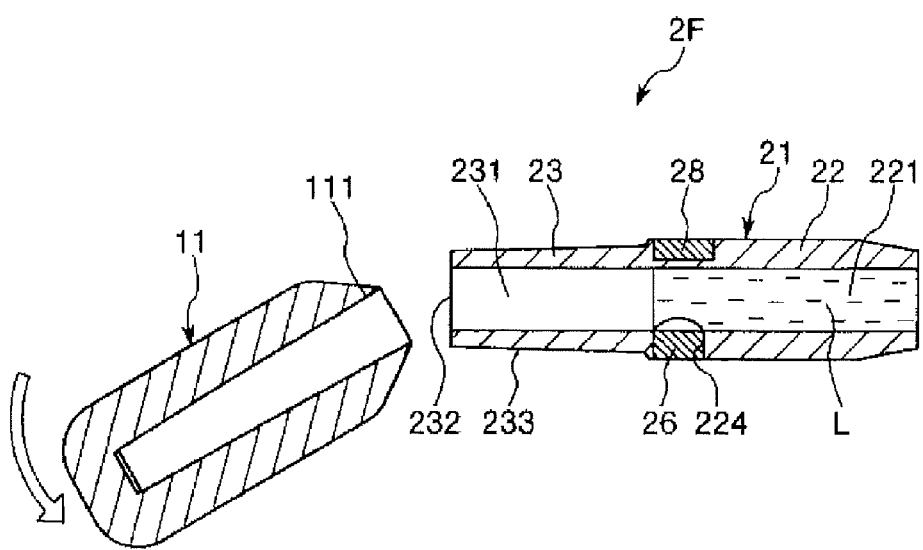
FIG. 27 is a view (a longitudinal sectional view) for sequentially illustrating the operation process of the connector (fifth embodiment) according to the present invention.

After the color change of the color change section 28 has been confirmed, the tube 30 is sealed by the clamp 40, and the click chip 11 is ruptured and removed from the liquid discharge port 23 of the connector 2F (see FIG. 27). As a result, the opening section 232 of the liquid discharge port 23 becomes unsealed.

[F3]

Figure 28:
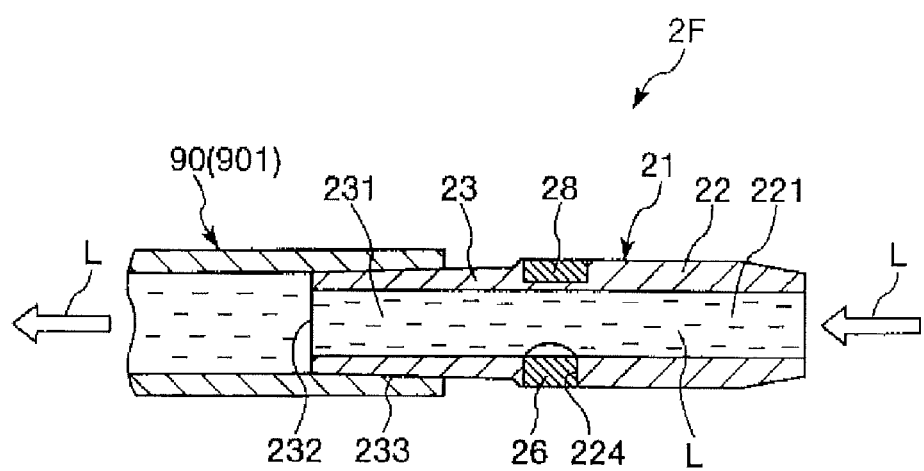
FIG. 28 is a view (a longitudinal sectional view) for sequentially illustrating an operation process of the connector (fifth embodiment) according to the present invention.

Immediately after removal of the click chip 11, the tubular section 901 of the connector 90 is connected to the liquid discharge port 23 of the connector 2F (see FIG. 28). When this connection is made, the inside of the second flow path 231 is filled up with air G, as discussed above, so that the medicinal liquid L in the connector 2F (first flow path 221) is securely prevented from leaking or scattering to the exterior from the second flow path 231. Consequently, the connection between the connector 2F and the connector 90 can be carried out safely.

In addition, once this connection is made, flow of the medicinal liquid L is resumed, and the medicinal liquid L flows from the connector 2F into the connector 90 (see FIG. 28).

While the connector and the infusion tube set according to the present invention have been described above while referring to embodiments shown in the drawings, the present invention is not limited to the embodiments. The components of the connector and the infusion tube set can be replaced by other arbitrary configurations, which are capable of exhibiting the same or similar functions. Arbitrary structures may also be added.

In addition, the connector and the infusion tube set according to the present invention may be a combination of any arbitrary two or more configurations (features) of the above-described embodiments.

Further, although in the above-described embodiments, a body, which is to be connected to the liquid discharge port of the connector according to the present invention, has been described as a tubular section of another connector, the invention is not limited to this feature. For example, the body to be connected to the liquid discharge part may be an end portion of a tube.

In addition, although in the connectors in the third to fifth embodiments the lock member is omitted in the configurations shown in the drawings, the invention is not limited by this feature, and the lock member may be disposed in the same manner as in the connector of the first embodiment.

INDUSTRIAL APPLICABILITY

The connector according to the present invention includes an inlet port into which a liquid is poured, and which has a first flow path through which the poured liquid passes, a liquid discharge port to which a tube body can be connected, and which has a second flow path through which the liquid having passed through the first flow path is discharged into the connected tube, gas discharge means, which discharges air in the first flow path when the liquid is poured into the first flow path, and blocking means, which, when the liquid is poured into the first flow path, temporarily stops flow of the liquid before the poured liquid reaches the second flow path. The connector is used in such a manner that an opening section of the liquid discharge port is sealed, the liquid is poured into the inlet port with the tube body not yet connected to the liquid discharge port, thereby causing air in the first flow path to be discharged through the gas discharge means. Then, while flow of the liquid is temporarily stopped in the first flow path by the blocking means, the opening section of the liquid discharge port is unsealed while flow of the liquid is temporarily stopped, the tube body is connected to the liquid discharge port, and flow of the liquid is resumed. Therefore, when a tube body is connected to the liquid discharge port of the connector in a condition in which, for example, a tube is preliminarily connected to the inlet port of the connector, and the inside of a portion ranging from the tube to the connector is filled with liquid, it is possible to securely prevent such liquid from leaking or scattering from the liquid discharge port. In addition, after connection of the tube body, transporting of the liquid into the tube body, which is connected to the discharge port, can be carried out speedily. Accordingly, the connector of the present invention has industrial applicability.

The invention claimed is:

1. A connector comprising:
   an inlet port into which a liquid is poured and which has a first flow path through which the poured liquid passes;
   a liquid discharge port to which a tube body can be connected and which has a second flow path through which the liquid having passed through the first flow path is discharged into the connected tube;
   a gas discharge means that discharges air contained in the first flow path when the liquid is poured into the first flow path;
   blocking means configured to stop flow of the liquid before the poured liquid reaches the second flow path when the liquid is poured into the first flow path, the blocking means including the gas discharge means; and
   a connector body disposed between the first flow path and the second flow path, the connector body including the gas discharge means and the blocking means;
   wherein the gas discharge means comprises a gas discharge port having a third flow path through which the air passes; and
   wherein the gas discharge means is configured to facilitate filling the first flow path entirely with the liquid and to temporarily stop flow of the liquid, when the liquid is poured into the first flow path in a state where the blocking means is capable of stopping the flow of the liquid before the liquid having passed through the first flow path reaches the second flow path.

2. The connector according to claim 1, wherein the second flow path is filled with air in a condition where flow of the liquid is temporarily stopped.

3. The connector according to claim 1, wherein a filter member, which is permeable to air but impermeable to liquid, is disposed in the third flow path.

4. The connector according to claim 1,
   wherein the first flow path, the second flow path and the third flow path intersect one another through an intersection part where end portions thereof intersect one another; and
   the blocking means is formed at the intersection part, and is comprised of a cylinder section, which is cylindrical in shape, and a cock, which is inserted turnably in the cylinder section and is formed with changeover flow paths corresponding to the flow paths, wherein opening and closing of the flow paths are selected by turning the cock.

5. The connector according to claim 1,
   wherein the blocking means has a valve body, which is disposed at the opening section of the liquid discharge port, and which has an opening/closing section being opened/closed so that the opening section can be sealed/unsealed through deformation; and
   the valve body is configured such that air is enclosed in the second flow path when the first flow path is filled with the liquid, in a condition where the opening/closing section is closed, and the opening/closing section is pushed by the tube body so as to be deformed and placed in an open state when the tube body is connected to the liquid discharge port.

6. The connector according to claim 1, wherein the gas discharge means is configured to facilitate filling the first flow path entirely with the liquid from the inlet port to the blocking means.

7. An infusion tube set comprising:
   a connector comprising:
      an inlet port into which a liquid is poured and which has a first flow path through which the poured liquid passes;
      a liquid discharge port to which a tube body can be connected and which has a second flow path through which the liquid has passed through the first flow path is discharged into the connected tube;
      a gas discharge means that discharges air contained in the first flow path when the liquid is poured into the first flow path; and
      blocking means configured to stop flow of the liquid before the poured liquid reaches the second flow path when the liquid is poured into the first flow path, the blocking means including the gas discharge means; and
      a connector body disposed between the first flow path and the second flow path, the connector body including the gas discharge means and the blocking means;
      wherein the gas discharge means comprises a gas discharge port having a third flow path through which the air passes; and
      wherein the gas discharge means is configured to facilitate filling the first flow path entirely with the liquid and to temporarily stop flow of the liquid, when the liquid is poured into the first flow path in a state where the blocking means is capable of stopping the flow of the liquid before the liquid having passed through the first flow path reaches the second flow path;
   a bag-side connector having two mutually independent flow paths provided at an inside thereof, a bag-side connection section, at which ends on one side of the two flow paths are opened, and which is connected to an infusion bag, and a tube connection section, which is provided at another end of one of the two flow paths, and to which a tube can be connected; and
   wherein the tube is connected at one end thereof to the inlet port of the connector, and is connected at another end thereof to the tube connection section of the bag-side connector.

8. The connector according to claim 7, wherein the gas discharge means is configured to facilitate filling the first flow path entirely with the liquid from the inlet port to the blocking means.

* * * * *